(12) United States Patent
Erickson et al.

(10) Patent No.: US 11,311,539 B2
(45) Date of Patent: *Apr. 26, 2022

(54) COMPOSITIONS AND METHODS FOR TREATMENT OF FRAGILE X SYNDROME

(71) Applicant: Children's Hospital Medical Center, Cincinnati, OH (US)

(72) Inventors: Craig Erickson, Cincinnati, OH (US); Tori Lynn Schaefer, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 201 days.

This patent is subject to a terminal disclaimer.

(21) Appl. No.: 16/703,935

(22) Filed: Dec. 5, 2019

(65) Prior Publication Data

US 2020/0121682 A1 Apr. 23, 2020

Related U.S. Application Data

(63) Continuation of application No. 16/194,625, filed on Nov. 19, 2018, now Pat. No. 10,588,905, which is a continuation of application No. 15/818,850, filed on Nov. 21, 2017, now Pat. No. 10,159,673, which is a continuation of application No. 14/994,705, filed on Jan. 13, 2016, now Pat. No. 9,844,551.

(60) Provisional application No. 62/103,126, filed on Jan. 14, 2015.

(51) Int. Cl.
*A61K 31/502* (2006.01)
*A61K 31/5025* (2006.01)

(52) U.S. Cl.
CPC ........ *A61K 31/5025* (2013.01); *A61K 31/502* (2013.01)

(58) Field of Classification Search
None
See application file for complete search history.

(56) References Cited

U.S. PATENT DOCUMENTS

| | | | |
|---|---|---|---|
| 4,994,467 | A | 2/1991 | Zimmerman |
| 5,084,278 | A | 1/1992 | Mehta |
| 5,098,715 | A | 3/1992 | McCabe et al. |
| 6,399,608 | B1 | 6/2002 | Dawson |
| 7,425,556 | B2 * | 9/2008 | Chapdelaine ........... A61P 25/24 514/248 |
| 9,066,949 | B2 | 6/2015 | Conour |
| 9,439,906 | B2 | 9/2016 | Vermeulen et al. |
| 9,610,259 | B2 | 4/2017 | Erickson et al. |
| 9,844,551 | B2 | 12/2017 | Erickson et al. |
| 10,098,854 | B2 | 10/2018 | Drevets et al. |
| 10,159,673 | B2 | 12/2018 | Erickson et al. |
| 10,350,159 | B2 | 7/2019 | Gutierro Aduriz et al. |
| 2004/0092534 | A1 | 5/2004 | Yam et al. |
| 2009/0048348 | A1 | 2/2009 | Chez |
| 2010/0159033 | A1 | 6/2010 | Gant et al. |
| 2014/0093592 | A1 | 4/2014 | Singh et al. |
| 2017/0095429 | A1 | 4/2017 | Erickson et al. |
| 2019/0083493 | A1 | 3/2019 | Erickson et al. |
| 2019/0321367 | A1 | 10/2019 | Erickson et al. |

FOREIGN PATENT DOCUMENTS

| | | |
|---|---|---|
| EP | 1567145 B1 | 8/2005 |
| WO | WO 1999/037303 A1 | 7/1999 |
| WO | WO 2004/045601 A1 | 6/2004 |
| WO | WO 2007/111880 A2 | 10/2007 |
| WO | WO 2009/109993 A1 | 9/2009 |
| WO | WO 2010/026254 A1 | 3/2010 |
| WO | WO 2012/123819 A1 | 9/2012 |
| WO | WO 2014/143646 A1 | 9/2014 |

OTHER PUBLICATIONS

Ciaccio, C. et al., Ital. J Pediatrics 2017 vol. 43 pp. 1-1.*
Lozano., R. et al., Intractable & Rare Dis Res 2016 vol. 5, pp. 145-157.*
Tsiouris, J. et al., CNS Drugs 2004, vol. 18, pp. 687-700.*
El Idrissi, A. et al., chapter in Adv. Exp. Med. Biol., Azuma, J, ed., New York, Springer, 2009 pp. 191-198.*
De Saint Jan, D. et al., J. Physiol. 2001 vol. 535.3, pp. 741-755.*
Pedapati, E., et al., "Gene Therapy Translational Studies for Fragile X Syndrome," FRAXA Research Foundation, Jun. 2019, downloaded from https://www.fraxa.org/gene-therapy-translational-studies-for-fragile-x-syndrome/, 6 pgs.
Canadian Office Action dated Sep. 22, 2020 for Application No. CA 2,936,809, 6 pgs.
Canadian Office Action dated May 10, 2021 for Application No. CA 2,936,809, 4 pgs.
European Search Report, Supplementary, and Written Opinion dated Oct. 23, 2020 for Application No. EP 17873707.8, 20 pgs.
Alhambra, C., et al., "Development and SAR of functionally selective allosteric modulators of GABA A receptors," Bioorganic & Medicinal Chemistry, 2011, 19:2927-38, 12 pgs.
Andrade, C., "Selective Serotonin Reuptake Inhibitor Drug Interactions in Patients Receiving Statins," J Clin Psychiatry, 2014, 75(2):e95-e99, Abstract Only, 1 pg.

(Continued)

*Primary Examiner* — Heidi Reese
(74) *Attorney, Agent, or Firm* — Frost Brown Todd LLC; Nicole M. Tepe

(57) ABSTRACT

Disclosed are methods of alleviating or preventing one or more symptoms associated with fragile X syndrome in an individual in need thereof via administration of a therapeutically effective amount of a GABA(A) alpha 2 and/or 3 partial agonist. The one or more symptoms may include impaired functional communication, anxiety, inattention, hyperactivity, sensory reactivity, autonomic nervous system dysregulation, aberrant eye gaze, self-injury, aggression, seizures, EEG abnormalities, including but not limited to, abnormal spectral analysis, event related potentials which may include auditory and visual responses, abnormalities in cortical responses as evoked by transcranial magnetic stimulation including resting and active motor thresholds and abnormal responses in measures of cortical inhibition and excitation, aberrant impaired cognitive function, compromised daily living skills, or a combination thereof.

12 Claims, 3 Drawing Sheets

(56) References Cited

OTHER PUBLICATIONS

Angkustsiri, K., et al., "Fragile X Syndrome with Anxiety Disorder and Exceptional Verbal Intelligence," Am J Med Genet Part A, 2008, 146:376-9, 4 pgs.
Atack, J.R., et al., "TPA023 [7-(1,1-Dimethylethyl)-6-(2-ethyl-2H-1,2,4-triazol-3-ylmethoxy)-3-(2-fluorophenyl)-1,2,4-triazolo[4,3-b]pyridazine], an Agonist Selective for α2- and α3-Containing $GABA_A$ Receptors, Is a Nonsedating Anxiolytic in Rodents and Primates," The Journal of Pharmacology and Experimental Therapeutics, 2006, 316(1):410-422, 13 pgs.
Bailey, Jr., D.B., et al., "Medication Utilization for Targeted Symptoms in Children and Adults with Fragile X Syndrome: US Survey," Journal of Developmental and Behavioral Pediatrics, 2012, 33:62-9, 8 pgs.
Berry-Kravis, E., et al., Psychopharmacology in Fragile X Syndrome—Present and Future, Ment Retard Dev Disabil Res Rev, 2004, 10:42-8, 7 pgs.
Berry-Kravis, E.M., et al., "Effects of STX209 (Arbaclofen) on Neurobehavioral Function in Children and Adults with Fragile X Syndrome: A Randomized, Controlled, Phase 2 Trial," Sci Transl Med, 2012, vol. 4, issue 152, 8 pgs.
Bhattacharya, A., et al., "Genetic Removal of p70 S6 Kinase 1 Corrects Molecular, Synaptic, and Behavioral Phenotypes in Fragile X Syndrome Mice," Neuron 2012, 76(2):325-37, 24 pgs.
Bourin, M., et al. "The mouse light/dark box test," European Journal of Pharmacology, 2003, 463:55-65, 11 pgs.
Brunskill, E.W., et al., "Abnormal neurodevelopment, neurosignaling and behaviour in Npas3-deficient mice," Eur J Neurosci, 2005, 22:1265-76, 12 pgs.
Chen, L., et al., "Fragile X Mice Develop Sensory Hyperreactivity To Auditory Stimuli," Neuroscience, 2001, 103(4):1043-50, 8 pgs.
Ciaccio, C., et al., "Fragile X syndrome: a review of clinical and molecular diagnoses," Ital. J. Pediatrics, 2017, 43(3( ):1-12, 12 pgs.
Crawley, J., et al., "Preliminary Report of a Simple Animal Behavior Model for the Anxiolytic Effects of Benzodiazepines," Pharmacol Biochem Behav, 1980, 13:167-70, 4 pgs.
Curran, C.P., et al., "In Utero and Lactational Exposure to PCBs in Mice: Adult Offspring Show Altered Learning and Memory Depending on Cypla2 and Ahr Genotypes," Environ Health Perspect, 2011, 119:1286-93, 8 pgs.
Dahlhaus, R., et al., "Altered neuroligin expression is involved in social deficits in a mouse model of the fragile X syndrome," Behavioural Brain Research, 2010, 208:96-105, 10 pgs.
De Saint Jan, D., et al., "Activation of human α1 and α2 homomeric glycine receptors by taurine and GABA," J. Physiol. 2001, 535. 3:741-755, 15 pgs.
D'Hooge, R., et al., "Mildly Impaired Water Maze Performance in Male Fmr1 Knockout Mice," Neuroscience, 1997, 76(2):367-76, 10 pgs.
D'Hulst. C., et al., "Decreased expression of the $GABA_A$ receptor in fragile X syndrome," Brain Research, 2006, 1121:238-45, 8 pgs.
D'Hulst, C., et al., "Expression of the GABAergic system in animal models for fragile X syndrome and fragile X associated tremor/ataxia syndrome (FXTAS)," Brain Research, 2009, 1253:176-83, 8 pgs.
D'Hulst, C., et al., "The GABAA receptor: a novel target for treatment of fragile X?", Trends in Neurosciences, 2007, 30(8):425-31, 7 pgs.
Dunlop, B.W., et al., "Tiagabine for social anxiety disorder," Human Psychopharmacology, 2007, 22:241-4, 4 pgs.
Egashira, N., et al., "Effects of mood stabilizers on marble-burying behavior in mice: Involvement of GABAergic system," Psychopharmacology, 2013, 226:295-305, 12 pgs.
El Idrissi, A., et al., "Decreased $GABA_A$ receptor expression in the seizure-prone fragile X mouse," Neuroscience Letters, 2005, 377:141-6, 6 pgs.
El Idrissi, A., et al., "Neuroendocrine Alterations in the Fragile X Mouse," Chapter 11, *Results Probl Cell Differ*, 2012, 54:201-21, 21 pgs.
El Idrissi, A., et al., "Taurine Improves Congestive Functions in a Mouse Model of Fragile X Syndrome," Adv Exp Med Biol, 2009, pp. 191-198, 1 pg. Abstract only.
Erickson, C.A., et al., "Managing maladaptive behaviors in fragile X patients," Curr Psychiatry, 2006, 5(10):80-92, 8 pgs.
Fragile X Syndrome, National Fragile X Foundation, downloaded Jul. 31, 2017 from https://fragilex.org/fragile-x/fragile-x-syndrome/, 2 pgs.
Frankland, P.W., et al., "Sensorimotor gating abnormalities in young males with fragile X syndrome and Fmr1-knockout mice," Molecular Psychiatry, 2004, 9:417-25, 9 pgs.
Garber, K.B., et al., "Fragile X syndrome," Eur J Hum Genet., Jun. 2008, 16(6):666-72, 14 pgs.
Gibb, R., et al., "A method for vibratome sectioning of Golgi-Cox stained whole rat brain," Journal of Neuroscience Methods, 1998, 79:1-4, 4 pgs.
Goebel-Goody, S.M., et al., "Genetic manipulation of STEP reverses behavioral abnormalities in a fragile X syndrome mouse model," Genes, Brain, and Behavior, 2012, 11:586-600, 15 pgs.
Goldson, E., et al., "The Fragile X Syndrome," Development Medicine and Child Neurology, 1992, 34:822-32, 7 pgs.
Hagerman, R.J., et al., "Fragile X Syndrome and Selective Mutism," Am J Med Genet, 1999, 83:313-7, 5 pgs.
Hagerman, R.J., et al., "Psychopathology in Fragile X Syndrome," The American Journal of Orthopsychiatry, 1989, 59(1):142-52, 11 pgs.
Hall, S., et al., "Effects of intranasal oxytocin on social anxiety in males with fragile X syndrome," Psychoneuroendocrinology, 2012, 37:509-518, 10 pgs.
Henderson, C., et al., "Reversal of Disease-Related Pathologies in the Fragile X Mouse Model by Selective Activation of $GABA_B$ Receptors with Arbaclofen," Science Translational Medicine, 2012, vol. 4, issue 152, 11 pgs.
Heulens, I., et al., "Involvement and Therapeutic Potential of the GABAergic System in the Fragile X Syndrome," TheScientificWorldJournal, 2010, 10:2198-206, 9 pgs.
Heulens, I., at al., "Pharmacological treatment of fragile X syndrome with GABAergic drugs in a knockout mouse model," Behav Brain Res., 2012, 229:244-249, 6 pgs.
Hochberg, Y., et al., "More Powerful Procedures for Multiple Significance Testing," Statistics in Medicine, 1990, 9:811-8, 8 pgs.
Hong, A., et al., "Downregulation of $GABA_a$ β Subunits is Transcriptionally Controlled by Fmr1p," J Mol Neurosci, 2012, 46:272-5, 4 pgs.
Jacquemont, S., et al., "Epigenetic Modification of the FMRI Gene in Fragile X Syndrome Is Associated with Differential Response to the mGluR5 Antagonist AFQ056," Science Translational Medicine, 2011, vol. 3, issue 64, 11 pgs.
Kooy, R.F., et al., "Transgenic Mouse Model for the Fragile X Syndrome" Am J Med Genet, 1996, 64:241-5, 5 pgs.
Kuribara, H., et al., "Assessment of the anxiolytic and amnesic effects of three benzodiazepines, diazepam, alprazolam and triazolam, by conflict and non-matching to sample tests in mice," Nihon shinkei seishin yakurigaku zasshi = Japanese Journal of Psychopharmacology, 1997, 17(1): 1-6. Abstract only, 1 pg.
Lindzey, G., et al., "Social dominance in inbred mouse strains," Nature, 1961, 191(4787):474-6. Bibliography only, 1 pg.
Liu, Z.H., et al., "Dissociation of social and nonsocial anxiety in a mouse model of fragile X syndrome," Neuroscience Letters, 2009, 454(1):62-6, 9 pgs.
Lozano, R, et al., "Fragile X syndrome: A review of clinical management," Intractable & Rare Dis Res, 2016, 5:145-157, 13 pgs.
Mientjes, E.J., et al., "The generation of a conditional Fmr1 knock out mouse model to study Fmrp function in vivo," Neurobiology of Disease, 2006, 21:549-55, 7 pgs.
Moon, J., et al., "Attentional Dysfunction, Impulsivity, and Resistance to Change in a Mouse Model of Fragile X Syndrome," Behavioral Neuroscience, 2006, 120(6):1367-79, 13 pgs.
Olmos-Serrano. J.L., et al., "The $GABA_A$ Receptor Agonist THIP Ameliorates Specific Behavioral Deficits in the Mouse Model of Fragile X Syndrome," Developmental Neuroscience, 2011, 33:395-403, 9 pgs.

(56) References Cited

OTHER PUBLICATIONS

Olmos-Serrano, J.L., et al., "Defective GABAergic Neurotransmission and Pharmacological Rescue of Neuronal Hyperexcitability in the Amygdala in a mouse Model of Fragile X Syndrome," The Journal of Neuroscience, 2010, 30(29):9929-38, 10 pgs.
Onaka, T., et al., "Roles of Oxytocin Neurones in the Control of Stress, Energy Metabolism, and Social Behavior," Journal of Neuroendocrinology, 2012, 24:587-598, 12 pgs.
Romero-Zerbo, Y., et al., "Protective effects of melatonin against oxidative stress in Fmr1 knockout mice: a therapeutic research model for the fragile X syndrome," Journal of Pineal Research, 2009, 46:224-34, 11 pgs.
Rudolph, U., et al., "Beyond classical benzodiazepines: Novel therapeutic potential of $GABA_A$ receptor subtypes," Nature Reviews Drug Discovery, 2011, 10(9):685-97, 26 pgs.
Schaefer, T.L., et al., "Targeted Mutations in the Na,K-ATPase Alpha 2 Isoform Confer Ouabain Resistance and Result in Abnormal Behavior in Mice," Synapse, 2011, 65:520-31, 12 pgs.
Schaefer, T.L., et al., "Mouse Pet-1 knock-out induced 5-HT disruption results in a lack of cognitive deficits and an anxiety phenotype complicated by hypoactivity and defensiveness," Neuroscience, 2009, 164(4):1431-43, 23 pgs.
Shanahan, M., et al., "Early temperament and negative reactivity in boys with fragile X syndrome," J Intellect Disabil Res, 2008, 52(part 10):842-54, 13 pgs.
Shimono, K., et al., "Long-term Recording of LTP in Cultured Hippocampal Slices," Neural Plasticity, 2002, 9(4):249-54, 6 pgs.
Sholl, D.A., *The Organization of the Cerebral Cortex*, London: Methuen & Co., 1956, 6 pgs.
Skelton, M.R., et al., "Creatine Transporter (CrT; Slc6a8) Knockout Mice as a Model of Human CrT Deficiency," PLoS One, 2011, 6(1):e16187, 11 pgs.
Sobesky, W.E., et al., "Emotional and neurocognitive deficits in fragile X," Am J Med Genet, 1994, 51:378-85, 8 pgs.
Spencer, C.M., et al., "Altered anxiety-related and social behaviors in the Fmr1 knockout mouse model of fragile X syndrome," Genes Brain Behav, 2005, 4:420-30, 11 pgs.
Thomas, A., et al., "Marble burying reflects a repetitive and perseverative behavior more than novelty-induced anxiety," Psychopharmacology (Berl), 2009, 204(2):361-73, 22 pgs.
Thomas, A.M., et al., "Group I metabotropic glutamate receptor antagonists alter select behaviors in a mouse model for fragile X syndrome," Psychopharmacology, 2012, 219:47-58, 13 pgs.
Tranfaglia, M.R., "Fragile X Syndrome: A Psychiatric Perspective," Chapter 16, *Results Probl Cell Differ*, 2012, 54:281-95, 16 pgs.
Tsiouris, J., et al., "Neuropsychiatric Symptoms of Fragile X Syndrome," CNS Drugs, 2004, 18(11):687-703, 17 pgs.
Veeraragavan, S., "Genetic reduction of muscarinic $M_4$ receptor modulates analgesic response and acoustic startle response in a mouse model of fragile X syndrome (FXS)," Behavioural Brain Research, 2012, 228(1):1-8, 22 pgs.
Williams, M.T., et al., "Neonatal methamphetamine administration induces regionspecific long-term neuronal morphological changes in the rat hippocampus, nucleus accumbens and parietal cortex," The European Journal of Neuroscience, 2004, 19:3165-70, 6 pgs.
Zhou, D., et al., "A clinical study to assess CYP1A2 and CYP3A4 induction by AZD7325, a selective $GABA_A$ receptor modulator—an in vitro and in vivo comparison," Br J Clin Pharmacol, 2012, 74(1):98-108, 11 pgs.
Aan Het Rot, M., et al., "Ketamine for depression: where do we go from here?" Biol Psychiatry, Oct. 1, 2012, 72(7):537-547, 18 pgs.
Adler, B.A., et al., "Drug-refractory aggression, self-injurious behavior, and severe tantrums in autism spectrum disorders: A chart review study," Autism, Jan. 2015, 19(1):102-106, 5 pgs.
Alphs, L., et al., "Real-World Outcomes of Paliperidone Palmitate Compared to Daily Oral Antipsychotic Therapy in Schizophrenia: A Randomized, Open-Label, Review Board-Blinded 15-Month Study," J Clin Psychiatry, 2015, 76(5):554-561, 13 pgs.

Aman, M.G., et al., "The Aberrant Behavior Checklist-Community: Factor Validity and Effect Of Subject Variables for Adults in Group Homes," American Journal on Mental Retardation, 1995, 100(3):283-292, 10 pgs.
American Psychiatric Association. *Autism Spectrum Disorder; Diagnostic and Statistical Manual of Mental Disorders, Fifth Edition*. Arlington, VA: American Psychiatric Association; 2013, 2 pgs.
Armstrong, T., et al., "Eye tracking of attention in the affective disorders: a meta-analytic review and synthesis", Clin Psychol Rev, 2012, 32(8):704-723 20 pgs.
Aylward, E.H., et al., "Effects of age on brain volume and head circumference in autism," Neurology, Jul. 23, 2002, 59(2):175-183, 9 pgs.
Bailey, A.R., et al., "Peripheral biomarkers in Autism: secreted amyloid precursor protein-alpha as a probable key player in early diagnosis", Int J Clin Exp Med, 2008, 1(4):338-344, 7 pgs.
Bailey, Jr., D.B., et al., "Autistic Behavior, FMRI Protein, and Developmental Trajectories in Young Males with Fragile X Syndrome", J Autism Dev Disord, Apr. 2001, 31(2):165-174, 11 pgs.
Barger, S.W., et al., "Microglial activation by Alzheimer amyloid precursor protein and modulation by apolipoprotein E", Nature, Aug. 28, 1997, 388(6645): 878-881, 4 pgs.
Berecz, R., et al., "The Role of Cytochrome P450 Enzymes in the Metabolism of Risperidone and Its Clinical Relevance for Drug Interactions," Current Drug Targets, 2004, 5:573-579, 7 pgs.
Berm, E.J.J., et al., "Effects and cost-effectiveness of pharmacogenetic screening for CYP2D6 among older adults starting therapy with nortriptyline or venlafaxine: study protocol for a pragmatic randomized controlled trial (CYSCEtrial)," Trials, 2015, 16:37, 7 pgs.
Berman RM, et al., "Antidepressant Effects of Ketamine in Depressed Patients," Biol Psychiatry, Feb. 15, 2000, 47(4):351-354, 4 pgs.
Berwaerts, J., et al., "Efficacy and Safety of the 3-Month Formulation of Paliperidone Palmitate vs Placebo for Relapse Prevention of Schizophrenia: A Randomized Clinical Trial," JAMA Psychiatry, 2015, 72(8):830-839, 10 pgs.
Brentani, H., et al., "Autism spectrum disorders: an overview on diagnosis and treatment", Revista Brasileira de Psiquiatria, 2013, 35(Suppl 1):S62-S72, XP002738648, 11 pgs.
Buitelaar, J.K., "Why have drug treatments been so disappointing?" In: *Autism: Neural Basis and Treatment Possibilities*, 2003, 235-249, 8 pgs.
Bushell, T., et al., "Pharmacological characterization of a non-inactivating outward current observed in mouse cerebellar Purkinje neurons," Br J Pharmacol, 2002, 135(3):705-712, 8 pgs.
Cai, S., et al., "Paliperidone extended-release tablets in Chinese patients with schizophrenia: meta-analysis of randomized controlled trials," Neuropsychiatr Dis Treat, 2015, 11:1817-1834, 18 pgs.
Canuso, C.M., et al., "Paliperidone extended-release tablets in schizophrenia patients previously treated with risperidone," Int Clin Psychopharmacol, 2008, 23(4):209-215, 7 pgs.
Carr, D.B., et al., "Safety and efficacy of intranasal ketamine for the treatment of breakthrough pain in patients with chronic pain: a randomized, double-blind, placebo-controlled, crossover study," Pain, 2004, 108(1-2):17-27, 11 pgs.
Centers for Disease Control and Prevention, Autism Spectrum Disorder, Data and Statistics, 2014, http://www.cdc.gov/ncbddd/autism/data.html, 6 pgs.
Chadman, K.K.., "Fluoxetine but not risperidone increases sociability in the BTBR mouse model of autism," Pharmacol Biochem Behav, 2011, 97(3):586-594, 9 pgs.
Chen, L-Y., et al., "Cystitis associated with chronic ketamine abuse," Psychiatry Clin Neurosci, 2009; 63(4):591-594, 1 pg.
Christensen, K., et al., "Safety and efficacy of intranasal ketamine for acute postoperative pain," Acute Pain, 2007, 9(4):183-192, XP022364900, 10 pgs.
Cook, Jr., E.H., "Genetics of autism," Child Adolesc Psychiatr Clin N Am, 2001, 10(2):333-350, 10 pgs.
Courchesne, E., et al., "Brain overgrowth in autism during a critical time in development: implications for frontal pyramidal neuron and interneuron development and connectivity," Int J Dev Neurosci, Apr.-May 2005, 23(2-3):153-170, 18 pgs.

(56) References Cited

OTHER PUBLICATIONS

Courchesne, E., et al., "Evidence of Brain Overgrowth in the First Year of Life in Autism," JAMA, Jul. 16, 2003, 290(3):337-344, 8 pgs.

Courchesne, E., et al., "Unusual brain growth patterns in early life in patients with autistic disorder: An MRI study," Neurology, Jul. 24, 2001, 57(2):245-254, 10 pgs.

Crews, K.R., et al., "Clinical Pharmacogenetics Implementation Consortium Guidelines for Cytochrome P450 2D6 Genotype and Codeine Therapy: 2014 Update," Clin Pharmacol Ther, 2014, 95(4):376-382, 7 pgs.

Davidovitch, M., et al., "Head Circumference Measurements in Children With Autism," J Child Neurol, 1996, 11(5):389-393, 5 pgs.

De Leon, J., et al., "The CYP2D6 Poor Metabolizer Phenotype May Be Associated With Risperidone Adverse Drug Reactions and Discontinuation," J Clin Psychiatry, 2005, 66(1):15-27, 13 pgs.

De Leon, J., et al., "The Pharmacokinetics of Paliperidone Versus Risperidone," Psychosomatics, 2010, 51(2):80-88, 9 pgs.

Doble, A., "The pharmacology and mechamsm of action of riluzole," Neurology, 1996, 47(Suppl 4):S233-S241, 9 pgs.

Dunnenberger, H.M., et al., "Preemptive Clinical Pharmacogenetics Implementation: Current Programs in Five US Medical Centers," Annual Review of Pharmacology and Toxicology, 2015, 55:89-106, 21 pgs.

Erickson, C.A., et al., "A retrospective study of memantine in children and adolescents with pervasive developmental disorders," Psychopharmacology, 2007, 191(1):141-147, 8 pgs.

Erickson, C.A., et al., "Eye Tracking Utilizing Age Matched Social Scenes and Geometric Shapes," Conference Paper. Conference: 2014 International Meeting for Autism Research, May 2014, 4 pgs. Abstract Only.

Erickson, C.A., et al., "Glutamatergic function in autism," In: U. Heresco-Levy and D.C. Javitt (eds.), *Glutamate in Neuropsychiatric Disorders*, Trivandrum, Kerala, India: Research Signpost; 2008, 9 pgs.

Erickson, C.A., et al., "Impact of Acamprosate on Amyloid Precursor Protein in Youth with Idiopathic and Fragile X Syndrome-Associated Autism Spectrum Disorder," Paper presented at: American Academy of Child and Adolescent Psychiatry Annual Meeting, 2013, Orlando, Florida, 1 pg.

Erickson, C.A., et al., "Open-Label Memantine in Fragile X Syndrome," J Autism Dev Disord, 2009, 39:1629-1635, 8 pgs.

Erickson, C.A., et al., "Open-label riluzole in fragile X syndrome," Brain Res, 2011, 1380:264-270, 7 pgs.

Falck-Ytter, T., et al., "Eye tracking in early autism research," J Neurodev Disord, 2013, 5(1):28, 13 pgs.

Fernandez-Mayoralas, D.M., et al., "Treatment With Paliperidone in Children With Behavior Disorders Previously Treated With Risperidone: An Open-Label Trial," Clin Neuropharmacol, 2012, 35(5):227-230, 4 pgs.

Fleeman, N., et al., "The clinical effectiveness and cost-effectiveness of genotyping for CYP2D6 for the management of women with breast cancer treated with tamoxifen: a systematic review," Health Technol Assess, 2011, 15(33):1-102, 126 pgs.

Fumagalli, E., et al., "Riluzole enhances the activity of glutamate transporters GLAST, GLT1 and EAAC1," Eur J Pharmacol, 2008, 578(2-3):171-176, 6 pgs.

Fung, L.K., et al., "Pharmacologic Treatment of Severe Irritability and Problem Behaviors in Autism: A Systematic Review and Meta-analysis," Pediatrics, 2016, 137(s2):e20152851K, 12 pgs.

Gaedigk, A., et al., "The CYP2D6 Activity Score: Translating Genotype Information into a Qualitative Measure of Phenotype," Clinical Pharmacology & Therapeutics, 2008, 83(2):234-242, 9 pgs.

Gaietto, K., et al., "Eye Tracking Utilizing Age Matched Social Scenes and Geometric Shapes," Conference Paper. Conference: 2014 International Meeting for Autism Research, May 2014, 4 pgs. Abstract Only.

Gennaro, A.R., et al., (eds.), *Remington's Pharmaceutical Sciences*, 18th Edition, Mack Publishing Company, Easton, Pennsylvania, 1990, 8 pgs. Table of Contents Only.

Green, S.M., et al., "Clinical Practice Guideline for Emergency Department Ketamine Dissociative Sedation in Children," Ann Emerg Med, Nov. 2004, 44(5):460-471, 12 pgs.

Green, S.M., et al., "Clinical Practice Guideline for Emergency Department Ketamine Dissociative Sedation: 2011 Update," Ann Emerg Med, May 2011, 57(5):449-461, 13 pgs.

Green, S.M., et al., "Inadvertent Ketamine Overdose in Children: Clinical Manifestations and Outcome," Ann Emerg Med, Oct. 1999, 34(4 Pt 1):492-497, 6 pgs.

Green, S.M., et al., "Ketamine Sedation in Mentally Disabled Adults," Academic Emergency Medicine, Jan. 1999, 6(1):86-87, 2 pgs.

Green, S.M., et al., "Predictors of Airway and Respiratory Adverse Events With Ketamine Sedation in the Emergency Department: An Individual-Patient Data MetaAnalysis of 8,282 Children," Ann Emerg Med, Aug. 2009. 54(2):158-168, e151-154, 15 pgs.

Green, S.M., et al., "Predictors of Emesis and Recovery Agitation With Emergency Department Ketamine Sedation: An Individual-Patient Data Meta-Analysis of 8,282 Children," Ann Emerg Med, Aug. 2009, 54(2):171-180, e171-174, 14 pgs.

Greig, N.H., et al., "Selective butyrylcholinesterase inhibition elevates brain acetylcholine, augments learning and lowers Alzheimer β-amyloid peptide in rodent," PNAS USA, 2005, 102(47):17213-17218, 6 pgs.

Guy, W., *ECDEU Assessment Manual for Psychopharmacology*, National Institute of Mental Health, Revised 1976, Table of Contents Only, 5 pgs.

Hatton, D.D., et al., "Autistic Behavior in Children With Fragile X Syndrome: Prevalence, Stability, and the Impact of FMRP," Am J Med Genet Part A, 2006, 140(17):1804-1813, 10 pgs.

Hazlett, H.C., et al., "Early Brain Overgrowth in Autism Associated With an Increase in Cortical Surface Area Before Age 2 Years," Arch Gen Psychiatry, May 2011, 68(5):467-476, 10 pgs.

He, Y., et al. "Neuroprotective agent riluzole potentiates postsynaptic GABA(A) receptor function," Neuropharmacology, Feb. 2002, 42(2):199-209, 11 pgs.

Hellings, J.A., et al., "A Crossover Study of Risperidone in Children, Adolescents and Adults with Mental Retardation," Journal of Autism and Development Disorders, 2006, 36(3):401-411, 11 pgs.

Hellings, J., et al., "Is There a Connection between Autism and Bipolar Disorder?" Autism Speaks, 2014, downloaded from <www.autismspeaks.org/expert-opinion/there-commection-between-autism-and-bipolar-disorder>, 2 pgs.

Huge, V., et al., "Effects of low-dose intranasal (S)-ketamine inpatients with neuropathic pain," European Journal of Pain, 2010, 14(4):387-394, XP026985780, 8 pgs.

Hurko, O., et al., "Novel drug development for amyotrophic lateral sclerosis," J Neurol Sci, 2000, 180(1-2):21-28, 8 pgs.

Ibrahim, L., et al., "Rapid Decrease in Depressive Symptoms with an N-methyl-d-aspartate Antagonist in ECT-Resistant Major Depression," Prog Neuropsychopharmacol Biol Psychiatry, 2011, 35(4):1155-1159, 10 pgs.

Jolly-Tornetta, C., et al., "Regulation of Amyloid Precursor Protein Secretion by Glutamate Receptors in Human Ntera 2 Neurons (NT2N)*," J Biol Chem, 1998, 273(22):14015-14021, 8 pgs.

Julious, S., "Sample size of 12 per group rule of thumb for a pilot study," Pharmaceutical Statistics, 2005, 4:287-291, 5 pgs.

Kalk, N., et al., "The clinical pharmacology of acamprosate," Br J Clin Pharmacol, 2012, 2:315-323, 9 pgs.

Kavalali, E.T., et al., "Spontaneous Neurotransmission: An Independent Pathway for Neuronal Signaling?" Physiology, Feb. 2011, 26(1):45-53, 9 pgs.

Kim, S.H., et al., "Aberrant early-phase ERK inactivation impedes neuronal function in fragile X syndrome," PNAS USA, 2008, 105(11):4429-4434, 6 pgs.

King, B.H., et al., "Double-Blind, Placebo-Controlled Study of Amantadine Hydrochloride in the Treatment of Children With Autistic Disorder," J Am Acad Child Adolesc Psychiatry, Jun. 2001, 40(6):658-665, 8 pgs.

Kowalski, J.L., et al., "Paliperidone Palmitate in a Child with Autistic Disorder," Journal of Child and Adolescent Psychopharmacology, 2011, 21(5):491-493, 3 pgs.

(56) References Cited

OTHER PUBLICATIONS

Krystal, J.H., et al., "Rapid-acting glutamatergic antidepressants: the path to ketamine and beyond," Biol Psychiatry, Jun. 2013, 73(12):1133-1141, 20 pgs.

Lahiri, D.K., et al., "A Critical Analysis of New Molecular Targets and Strategies for Drug Developments in Alzheimer's Disease," Current Drug Targets, Feb. 2003, 4(2):97-112, 18 pgs.

Lahiri, D.K., et al., "Autism as early neurodevelopmental disorder: evidence for an sAPPα-mediated anabolic pathway.", Frontiers in Cellular Neuroscience, 2013, 7(94):1-13, 13 pgs.

Lahiri, D.K., et al., "Developmental Expression of the β-Amyloid Precursor Protein and Heat-Shock Protein 70 in the Cerebral Hemisphere Region of the Rat Brain," Ann N.Y. Acad Sci, Jun. 2002, 965:324-333, 10 pgs.

Lahiri, D.K., et al., "Tacrine Alters the Secretion of the Beta-Amyloid Precursor Protein in Cell Lines," J Neurosci Res, Apr. 1994, 37(6):777-787, 11 pgs.

Lahiri, D.K., et al., "The secretion of amyloid B-peptides is inhibited in the tacrine-treated human neuroblastoma cells," Brain Res Mol Brain Res, Nov. 1998, 62(2):131-140, 10 pgs.

Langaee, T., et al., "A Novel Simple Method for Determining CYP2D6 Gene Copy Number and Identifying Allele(s) with Duplication/Multiplication," PloS One, 2015, 10(1):e0113808, 11 pgs.

Leclerc, S., et al., "Pharmacological Therapies for Autism Spectrum Disorder: A Review," Pharmacy & Therapeutics, 2015, 40(6):389-397, 9 pgs.

Levitt, P., et al., "The genetic and neurobiologic compass points toward common signaling dysfunctions in autism spectrum disorders," J Clin Invest, Apr. 2009, 119(4):747-754, 8 pgs.

Malinovsky, J.M., et al., "Ketamine and norketamine plasma concentrations after i.v., nasal and rectal administration in children," Br J Anaesth, Aug. 1996, 77(2):203-207, 5 pgs.

Marcus, R.N., et al., "A Placebo-Controlled, Fixed-Dose Study of Aripiprazole in Children and Adolescents With Irritability Associated With Autistic Disorder," J. Am. Acad. Child Adolesc. Psychiatry, 2009, 48(11):1110-1119, 10 pgs.

Matson, J.L., et al., "The relationship of self-injurious behavior and other maladaptive behaviors among individuals with severe and profound intellectual disability," Research in Developmental Disabilities, 2008, 29(2): 141-148, 8 pgs.

Mattson, M.P., "Cellular Actions of β-Amyloid Precursor Protein and Its Soluble and Fibrillogenic Derivatives," Physiological Reviews, Oct. 1997, 77(4):1081-1132, 52 pgs.

Mattson, M.P., "Secreted Forms of β-Amyloid Precursor Protein Modulate Dendrite Outgrowth and Calcium Responses to Glutamate in Cultured Embryonic Hippocampal Neurons," J Neurobiol, Apr. 1994, 25(4):439-450, 12 pgs.

Mattson, M.P., et al., "Signaling Events Regulating the Neurodevelopmental Triad: Glutamate and Secreted Forms of β-Amyloid Precursor Protein as Examples," Perspectives on Developmental Neurobiology, 1998, 5(4):337-352, 16 pgs.

Mayer, S., et al., "Acamprosate Has No Effect on NMDA-Induced Toxicity But Reduces Toxicity Induced by Spermidine or by Changing the Medium in Organotypic Hippocampal Slice Cultures From Rat," Alcohol Clin Exp Res, May 2002, 26(5):655-662, 8 pgs.

McCaffery, P., et al., "Macrocephaly and the control of brain growth in autistic disorders," Prog Neurobiol, Sep.-Oct. 2005, 77(1-2):38-56, 19 pgs.

McClintock, K., et al., "Risk markers associated with challenging behaviors in people with intellectual disabilities: a meta-analytic study," Journal of Intellectual Disability Research, 2003, 47(6):405-416, 12 pgs.

McFarlane, H.G., et al., "Autism-like behavioral phenotypes in BTBR T+tf/J mice," Genes Brain Behav, Mar. 2008, 7(2):152-163, 12 pgs.

McGuire, K., et al., "Psychiatric Hospitalization of Children with Autism or Intellectual Disability: Consensus Statements on Best Practices," J Am Acad Child Adolesc Psychiatry, 2015, 54(12):969-971, 5 pgs.

Moy, S.S., et al., "Mouse Behavioral Tasks Relevant to Autism: Phenotypes of Ten Inbred Strains," Behav Brain Res, Jan. 2007, 176(1):4-20, 31 pgs.

Mullan, M., et al., "Genetic and molecular advances in Alzheimer's disease," Trends Neurosci, Oct. 1993, 16(10):398-403, 6 pgs.

Naassila, M., et al., "Mechanism of Action of Acamprosate. Part I. Characterization of Spermidine-Sensitive Acamprosate Binding Site in Rat Brain," Alcohol Clin Exp Res, Jun. 1998, 22(4):802-809, 8 pgs.

Nelson, D.R., et al., "P450 superfamily: update on new sequences, gene mapping, accession numbers and nomenclature," Pharmacogenetics, 1996, 6(1):1-42, 42 pgs.

Niebroj-Dobosz, I., et al., "Effect of Riluzole on serum amino acids in patients with amyotrophic lateral sclerosis," Acta Neurol Scand, Jul. 2002, 106(1):39-43, 5 pgs.

Nussbaum, A.M., et al., "Paliperidone Palmitate for Schizophrenia," Schizophrenia Bulletin, 2012, 38(6):1124-1127, 4 pgs.

Orser, B.A., et al., "Multiple Mechanisms of Ketamine Blockade of N-methyl-D-aspartate Receptors," Anesthesiology, Apr. 1997, 86(4):903-917, 15 pgs.

Owen, R., et al., "Aripiprazole in the Treatment of Irritability in Children and Adolescents With Autistic Disorder," Peiatrics, 2009, 124(6):1533-1540, 8 pgs.

Palucha-Poniewiera, A., et al., "Involvement of mGlu5 and NMDA receptors in the antidepressant-like effect of acamprosate in the tail suspension test," Prog Neuropsychopharmacol Biol Psychiatry, Oct. 2012, 39(1):102-106, 5 pgs.

Papolos, D.F., et al., "Clinical experience using intranasal ketamine in the treatment of pediatric bipolar disorder/fear of harm phenotype," J Affect Disord, May 2013, 147(1-3):431-436, 6 pgs.

Patsopoulos, N.A., et al., "CYP2D6 polymorphisms and the risk of tardive dyskinesia in schizophrenia: a meta-analysis," Pharmacogenet Genomics, 2005, 15(3):151-158, 8 pgs.

Posey, D., et al., "A Double-Blind, Placebo-Controlled Study of D-Cycloserine in Children with Autistic Disorder," Presentation at: 55th Annual Meeting of the American Academy of Child and Adolescent Psychiatry, 2008; Chicago, Illinois, Information Page only, 2 pgs.

Priller, C., et al., "Synapse Formation and Function is Modulated by the Amyloid Precursor Protein," J Neurosci, Jul. 2006, 26(27):7212-7221, 10 pgs.

Rainey, L., et al., "The Anaesthetic Management of Autistic Children," Anesthesia and Intensive Care, 1998, 26(6):682-686, XP009183694, 5 pgs.

Ray, B., et al., "Increased Secreted Amyloid Precursor Protein-α (sAPPβ) in Severe Autism: Proposal of a Specific, Anabolic Pathway and Putative Biomarker," PLoS ONE, 2011, 6(6):e20405, 10 pgs.

Robb, A.S., "Managing Irritability and Aggression in Autism Spectrum Disorders in Children and Adolescents," Developmental Disabilities Research Reviews, 2010, 16(3):258-264, 7 pgs.

Roberts, R.L., et al., "No evidence of increased adverse drug reactions in cytochrome P450 CYP2D6 poor metabolizers treated with fluoxetine or nortriptyline," Hum Psychopharmacol, 2004, 19(1):17-23, 7 pgs.

Savitz, A.J., et al., "Efficacy and Safety of Paliperidone Extended Release in Adolescents With Schizophrenia: A Randomized, Double-Blind Study," J Am Acad Child Adolesc Psychiatry, 2015, 54(2):126-137, 13 pgs.

Schubert, D., et al., "The Regulation of Amyloid β Protein Precursor Secretion and Its Modulatory Role in Cell Adhesion," Neuron, Dec. 1989, 3(6):689-694, 6 pgs.

Seeman, P., et al., "Memantine Agonist Action at Dopamine $D2^{High}$ Receptors," Synapse, Feb. 2008, 62(2):149-153, 5 pgs.

Shaffer, R.C., et al., "Brief Report: Diminished Gaze Preference for Dynamic Social Interaction Scenes in Youth with Autism Spectrum Disorders," J Autism Dev Disord, 2017, 47:506-513, 8 pgs.

Shea, S., et al., "Risperidone in the Treatment of Disruptive Behavioral Symptoms in Children With Autistic and Other Pervasive Developmental Disorders," Peidatrics, 2004, 114(5):e634-e641, 8 pgs.

(56) References Cited

OTHER PUBLICATIONS

Shi, C., et al., "Pharmacogenetics-Based versus Conventional Dosing of Warfarin: A Meta-Analysis of Randomized Controlled Trials," PloS One, 2015, 10(12):e0144511, 16 pgs.
Siegel, M., et al., "Specialized Inpatient Psychiatry for Serious Behavioral Disturbance in Autism and Intellectual Disability," J Autism Dev Disord, 2014, 44(12):3026-3032, 7 pgs.
Silverman, J.L., et al., "AMPAKINE enhancement of social interaction in the BTBR mouse model of autism," Neuropharmacology, Jan. 2013, 64:268-282, 29 pgs.
Silverman, J.L., et al., "Repetitive Self Grooming Behavior in the BTBR Mouse Model of Autism is Blocked by the mGluR5 Antagonist MPEP", Neuropsychopharmacology, Mar. 2010, 35(4):976-989, 14 pgs.
Sistonen, J., et al., "'CYP2D6 worldwide genetic variation shows high frequency of altered activity variants and no continental structure," Pharmacogenet Genomics, 2007, 17(2):93-101, 9 pgs.
Sokol, D.K., et al., "Autism, Alzheimer disease, and fragile X: APP, FMRP, and mGluR5 are molecular links," Neurology, Apr. 2011, 76(15):1344-1352, 9 pgs.
Sokol, D.K., et al., "High levels of Alzheimer Beta-Amyloid Precursor Protein (APP) in Children With Severely Autistic Behavior and Aggression," J Child Neurol, Jun. 2006, 21(6):444-449, 7 pgs.
Sparks, B.F., et al., "Brain structural abnormalities in young children with autism spectrum disorder," Neurology, Jul. 2002, 59(2):184-192, 9 pgs.
Stein, T.D., et al., "Genetic Programming by the Proteolytic Fragments of the Amyloid Precursor Protein: Somewhere Between Confusion and Clarity," Reviews in the Neurosciences, 2003, 14(4):317-341, 26 pgs.
Stigler, K.A., et al., "Paliperidone for Irritability in Autistic Disorder," Journal of Child and Adolescent Psychophamacology, 2010, 20(1):75-78, 4 pgs.
Stigler, K.A., et al., "Paliperidone for irritability in adolescents and young adults with autistic disorder," Psychopharmacology, 2012, 223(2):237-245, 9 pgs.
The Interagency Autism Coordinating Committee. 2010 Strategic Plan for Autism Spectrum Disorder Research. NIH Publication No. 10-7573: Department of Health & Human Services USA; 2010, 60 pgs.
The Interagency Autism Coordinating Committee. 2011 Strategic Plan for Autism Spectrum Disorder Research. NIH Publication No. 10-7573: Department of Health & Human Services USA; 2011, 105 pgs. [part 1 of 2, 56 pgs.; part 2 of 2, 49 pgs.].
Tottenham, N., et al., "Categorization of Facial Expressions in Children and Adults: Establishing a Larger Stimulus Set," Cognitive Neuroscience Society Annual Meeting, Apr. 15, 2002, p. 74, 1 pg.
Tottenham, N., et al., "The NimStim set of facial expressions: Judgments from untrained research participants," Psychiatry Research, 2009, 168(3):242-249, XP026322365, 8 pgs.
Turkoz, I., et al., "Paliperidone ER and oral risperidone in patients with schizophrenia: a comparative database analysis," BMC Psychiatry, 2011, 11:21, 10 pgs.
Turner, P.R., et al., "Roles of amyloid precursor protein and its fragments in regulating neural activity, plasticity and memory," Prog Neurobiol, May 2003, 70(1):1-32, 32 pgs.
Uenishi, H., et al., "Ion Channel Modulation as the Basis for Neuroprotective Action of MS-153," Ann N.Y. Acad Sci, 1999, 890:385-399, 15 pgs.
Vanwong, N., et al., "Impact of CYP2D6 Polymorphism on Steady-State Plasma Levels of Risperidone and 9-Hydroxyrisperidone in Thai Children and Adolescents with Autism Spectrum Disorder," Journal of Child and Adolescent Psychopharamacology, 2017, 27(2):185-191, 7 pgs.
Vuilleumier, P.H., et al., "Pharmacogenomic considerations in opioid analgesia," Pharmacogenomics and Personalized Medicine, 2012, 5:73-87, 15 pgs.
Wang, S.J., et al., "Mechanisms Underlying the Riluzole Inhibition of Glutamate Release From Rat Cerebral Cortex Nerve Terminals (Synaptosomes)," Neuroscience, 2004, 125(1):191-201, 11 pgs.
Weng, N., et al., "Early-Phase ERK Activation as a Biomarker for Metabolic Status in Fragile X Syndrome," Am J Med Genet B (Neuropsychiatr Genet), Oct. 2008. 147B(7):1253-1257, 5 pgs.
Westphalen, R.I., et al., "Selective Depression by General Anesthetics of Glutamate Versus GABA Release from Isolated Cortical Nerve Terminals," J Pharmacol Exp Ther, Mar. 2003, 304(3):1188-1196, 9 pgs.
Wink, L.K., et al., "Intranasal Ketamine Treatment in an Adult With Autism Spectrum Disorder," The Journal of Clinical Psychiatry, Aug. 2014, 75(8):835-836, XP009183695, 2 pgs.
Wink, L.K., et al., "Pharmacologic Treatment of Behavioral Symptoms Associated With Autism and Other Pervasive Developmental Disorders," Curr Treat Options Neurol, Nov. 2010, 12(6):529-538, 10 pgs.
Wong, S.W., et al., "Dilated common bile ducts mimicking choledochal cysts in ketamine abusers," Hong Kong Med J, Feb. 2009, 15(1):53-56, 4 pgs.
Yagihashi, T., et al., "Effects of the CYP2D6*10 alleles and co-medication with CYP2D6-dependent drags on risperidone metabolism in patients with schizophrenia," Human Psychopharmacology, 2009, 4:301-308, 1 pg. (Abstract Only).
Yang, M., et al., "Social Deficits in BTBR T+tf/J Mice are Unchanged by Cross-Fostering with C57BL/6J Mothers," Int J Dev Neurosci, Dec. 2007, 25(8):515-521, 14 pgs.
Young-Pearse, T.L., et al., "A Critical Function for β-Amyloid Precursor Protein in Neuronal Migration Revealed by In Utero RNA Interference," J Neurosci, Dec. 2007, 27(52):14459-14469, 11 pgs.
Youngster, I., et al., "CYP2D6 genotyping in paediatric patients with autism treated with risperidone: a preliminary cohort study," Developmental Medicine & Child Neurology, 2014, 56(10):990-994, 5 pgs.
Zarate, Jr., C.A., et al., "A Randomized Trial of an N-methyl-D-aspartate Antagonist in Treatment-Resistant Major Depression," Arch Gen Psychiatry, Aug. 2006, 63(8):856-864, 9 pgs.
Zarate, Jr., C.A., et al., "Replication of Ketamine's Antidepressant Efficacy in Bipolar Depression: A Randomized Controlled Add-on Trial," Biol Psychiatry, Jun. 2012, 71(11):939-946, 18 pgs.
Zhou, S-F., "Polymorphism of Human Cytochrome P450 2D6 and Its Clinical Significance: Part II," Clinical Pharmacokinetics, 2009, 48(12):761-804, 44 pgs.
European Communication, Intention to Grant, dated Oct. 18, 2018 for Application No. EP 15 702 607.1, 90 pgs.
European Communication dated Mar. 26, 2018 for Application No. EP 15 702 607.1, 4 pgs.
European Search Report, Partial Supplementary, and Provisional Written Opinion dated Jun. 9, 2020 for Application No. EP 17873707.8, 15 pgs.
International Search Report and Written Opinion dated May 7, 2015 for Application No. PCT/US2015/011412.
International Search Report and Written Opinion dated Jan. 24, 2018 for Application No. PCT/US2017/062696, 16 pgs.
U.S. Appl. No. 61/926,991, filed Jan. 14, 2014.
U.S. Appl. No. 62/059,306, filed Oct. 3, 2014.
U.S. Appl. No. 62/425,665, filed Nov. 23, 2016.

* cited by examiner

COMPOSITIONS AND METHODS FOR TREATMENT OF FRAGILE X SYNDROME

CROSS-REFERENCE TO RELATED APPLICATIONS

This application claims the benefit of U.S. application Ser. No. 16/194,625, filed Nov. 19, 2018, which claims the benefit of U.S. application Ser. No. 15/818,850 filed Nov. 21, 2017, now U.S. Pat. No. 10,159,673, issued on Dec. 25, 2018, which claims the benefit of U.S. application Ser. No. 14/994,705 filed Jan. 13, 2016, now U.S. Pat. No. 9,844,551, issued on Dec. 19, 2017, which claims the benefit of U.S. Application Ser. No. 62/103,126, filed Jan. 14, 2015, all of which are incorporated herein by reference in their entirety for all purposes.

BACKGROUND

Fragile X Syndrome (FXS) is the most common inherited form of developmental disability (DD), affecting 1 in 4,000 persons and is responsible for up to 2-6% of all cases of DD. FXS is also a common single gene cause of autism spectrum disorder (ASD).

BRIEF SUMMARY

Disclosed are methods of alleviating or preventing one or more symptoms associated with fragile X syndrome in an individual in need thereof via administration of a therapeutically effective amount of a GABA(A) alpha 2 and/or 3 partial agonist. The one or more symptoms may include impaired social and functional communication, anxiety, inattention, hyperactivity, altered sensory reactivity, self-injury, aggression, impaired cognitive function, compromised daily living skills, or a combination thereof.

BRIEF DESCRIPTION OF THE DRAWINGS

FIG. 4; top main effect of genotype (P<0.001) and drug (P<0.0001) for Vmax) shows that Fmr1 KO mice treated chronically with the low dose of AZD7325 have significantly reduced whole body flinching in this low-level Acoustic startle paradigm. Interestingly, in a paradigm employing a high level acoustic stimulus (120 dB), adult Fmr1 KO mice will repeatedly respond to the stimulus with a lower amplitude whole body flinch compared to WT mice. FIG. 4; bottom (Gene x Drug interaction P<0.0001) shows that treatment with AZD7325 improves this response to WT levels demonstrating that drug treatment isn't simply reducing overall whole body flinching in response to sensory stimuli, but is rather mediating responses so that they are becoming more appropriate and reflective of startle intensity. *P indicates significantly different from WT+VEH; #P indicates significantly different from KO+VEH.

DETAILED DESCRIPTION

Figure 1:
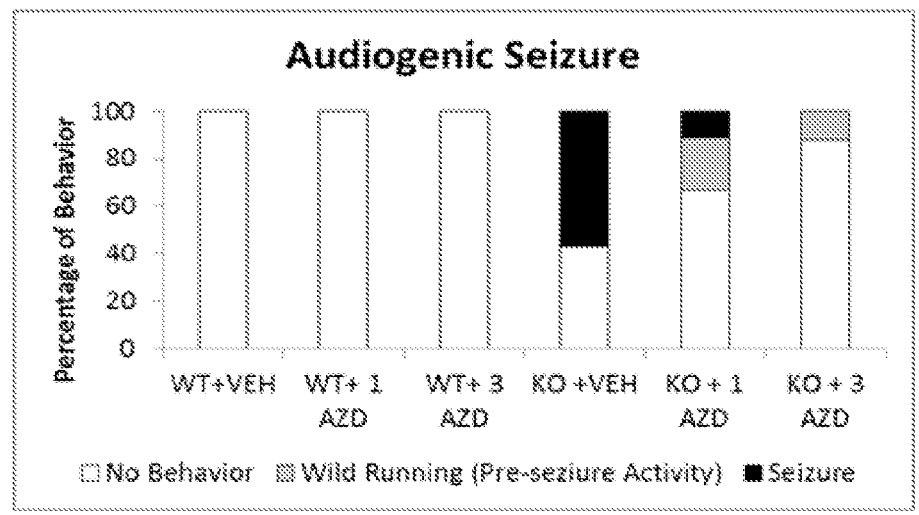
FIG. 1 shows that approximately 60% Fmr1 KO mice treated with VEH displayed wild running followed by seizure in response to a loud stimulus (120 dB siren), but when treated acutely (30 min prior to testing) with both the low (11%) and high (0%) dose of 4-amino-8-(2-fluoro-6-methoxy-phenyl)-N-propyl-cinnoline-3-carboxamide ("AZD7325"), seizure activity was significantly reduced, indicating that the drug is reducing hyperexcitability in the brain (Fisher's exact test p<0.0002).

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviations, per the practice in the art. Alternatively, "about" can mean a range of up to 20%, or up to 10%, or up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

"Dosage unit form" as used herein refers to physically discrete units suited as unitary dosages for the subject to be treated, each unit containing a predetermined quantity of active compound calculated to produce the desired therapeutic effect in association with the required pharmaceutical carrier. The specification for the dosage unit forms of the preferred embodiments are dictated by and directly dependent on the unique characteristics of the active compound and the particular therapeutic effect to be achieved, and the limitations inherent in the art of compounding such an active compound for the treatment of individuals.

The terms "individual," "host," "subject," and "patient" are used interchangeably to refer to an animal that is the object of treatment, observation and/or experiment. "Animal" includes vertebrates and invertebrates, such as fish, shellfish, reptiles, birds, and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans.

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. Pharmaceutically acceptable carriers include a wide range of known diluents (i.e., solvents), fillers, extending agents, binders, suspending agents, disintegrates, surfactants, lubricants, excipients, wetting agents and the like commonly used in this field. These carriers may be used singly or in combination according to the form of the pharmaceutical preparation, and may further encompass "pharmaceutically acceptable excipients" as defined herein.

As used herein, "pharmaceutically acceptable excipient" means any other component added to a pharmaceutical formulation other than the active ingredient and which is capable of bulking-up formulations that contain potent active ingredients (thus often referred to as "bulking agents," "fillers," or "diluents") to allow convenient and accurate dispensation of a drug substance when producing a dosage form. Excipients may be added to facilitate manufacture, enhance stability, control release, enhance product characteristics, enhance bioavailability drug absorption or solubility, or other pharmacokinetic considerations, enhance patient acceptability, etc. Pharmaceutical excipients include, for example, carriers, fillers, binders, disintegrants, lubricants, glidants, colors, preservatives, suspending agents, dispersing agents, film formers, buffer agents, pH adjusters, preservatives etc. The selection of appropriate excipients also depends upon the route of administration and the dosage form, as well as the active ingredient and other factors, and will be readily understood by one of ordinary skill in the art.

As used herein, the term "therapeutically effective amount" means the total amount of each active component of the pharmaceutical composition or method that is sufficient to show a meaningful patient benefit, e.g., healing of chronic conditions or in an increase in rate of healing of such conditions, or in a reduction in aberrant conditions. This includes both therapeutic and prophylactic treatments. Accordingly, the compounds can be used at very early stages of a disease, or before early onset, or after significant progression. When applied to an individual active ingredient, administered alone, the term refers to that ingredient alone. When applied to a combination, the term refers to combined amounts of the active ingredients that result in the therapeutic effect, whether administered in combination, serially or simultaneously.

FXS results from an expanded CGG triplet repeat expansion resulting in methylation and transcriptional silencing of the Fragile X Mental Retardation 1 gene and transcriptional silencing of the Fragile X Mental Retardation Protein (FMRP). FMRP is known to be an RNA binding protein responsible for translational control of hundreds of genes involved in various functions including, but not limited to, intracellular and synaptic signalling. Of the many genes known to be regulated by FMRP, the gamma-aminobutyric acid receptor A (GABA(A)) is gaining attention as a potential pharmacotherapy target for the treatment of FXS. Mounting evidence suggests decreased expression and functioning of GABA(A) is intimately involved in the pathophysiology of FXS. Non-selective GABA(A) agonism in animal models of FXS has been associated with the normalization of morphological features, GABA(A) expression, and some behavior. One down side of the nonselective nature of these agents is the increased likelihood of unwanted side-effects, such as sedation and dulling of cognition, which could impeded the long-term use of nonselective GABA(A) agonist pharmacotherapy in FXS. Benzodiazepines act as potent non-selective agonists across GABA(A) receptor subunits alpha 1, alpha 2, alpha 3, and alpha 5. Therefore, use of benzodiazepines is often limited in FXS given concerns over drug tolerability rooted in the sedating and potentially cognitively dulling features of this drug class. The sedating and amnesic effects of benzodiazepines are due to effects at alpha1 and alpha 5 subunit containing receptors, respectively.

Recent pre-clinical findings in Fragile X Syndrome knockout animal models have led to targeted treatment development efforts in this field. To date, drug development focused on metabotropic glutamate receptor type 5 (mGluR5) antagonists and a gamma-aminobutyric acid receptor B (GABA(B)) agonist have not been marked by a robust, universal drug effect. In both mGluR5 and GABA(B) human trials to date, only subsets of persons with FXS have potentially shown response with treatment but larger studies have failed to demonstrate efficacy over placebo. Given these finding, there is a clear need to explore unique mechanisms of treatment in this field. Increasing evidence has pointed to dysregulation of GABA(A) receptor (GABA(A)) neurotransmission in the pathophysiology of FXS. Among potential targets of drug therapy in FXS, modulation of GABA(A) activity, in particular selective agonism, remains largely unexplored in humans with FXS. Preclinical data implicating GABA(A) dysregulation in FXS includes evidence that Fragile X Mental Retardation Protein (FMRP) transcriptionally regulates GABA(A) receptor subunit RNA expression with reductions in GABA(A) receptor mRNA noted in FXS KO mice lacking FMRP, Additionally, GABA (A) receptor expression has been shown to be significantly down regulated in a number of brain regions in FXS KO mice that are important for behavior including the hippocampus and amygdala. In animal models of FXS, non-selective or extrasynaptic GABA(A) agonism has shown significant promise as a pharmacotherapy target. Regarding preclinical treatment, study of the GABA(A) agonist in FXS, alphaxalone, a neuroactive steroid with multiple potential pharmacodynamics effect including modulation of nicotinic acetylcholine receptors, activation of chloride channels, and non-selective GABA(A) agonism, was associated with reductions in anxiety and rescue of audiogenic seizures in FXS KO mice. Also in FXS KO mice, the GABA(A) extrasynaptic δ-subunit agonist gaboxadol restored neuron excitability deficits in the amygdala, reduced hyperactivity, and reduced prepulse inhibition (PPI) alterations. No studies published to date have assessed GABA(A) modulation via a specific alpha 2,3 partial agonist.

Given the limitations in available FDA approved GABA (A) focused treatments of FXS, Applicant has investigated a novel selective GABA(A) agonist in a mouse model of FXS. In one aspect, the novel agonist is a specific GABA(A) alpha2,3 partial agonist. In a further aspect, the compound is 4-amino-8-(2-fluoro-6-methoxy-phenyl)-N-propyl-cinnoline-3-carboxamide ("AZD7325"). Applicant has shown that, using the disclosed partial agonist, several key behavioral deficits in the Fmr1 KO mouse model are normalized or attenuated.

In one aspect, a method of alleviating or preventing one or more signs or symptoms of fragile X is disclosed. The method may comprise the step of administering to a subject in need thereof, a therapeutically effective amount of a GABA(A) alpha 2 and/or 3 partial agonist.

In one aspect, the GABA(A) alpha 2 and/or 3 agonist or partial agonist may act at the GABA(A) receptor site, and may have a lower binding affinity to and/or less efficacy of receptor activation at the GABA(A) alpha 1 subunit as compared to the binding affinity and/or receptor efficacy at the alpha 2 and/or alpha 3 subunit.

In one aspect, the GABA(A) alpha 2,3 agonist may be selected from

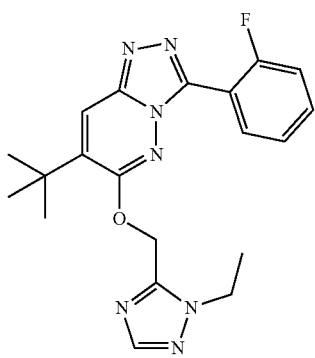
(TPA-023)

or a pharmaceutically acceptable salt thereof;

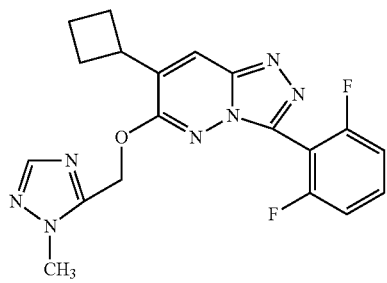
(MK-0343)

or a pharmaceutically acceptable salt thereof;

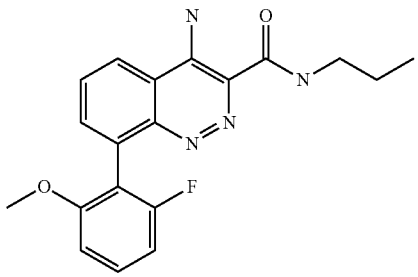 [SMILES: CCCNC(=O)c1nnc2c(-c3c(F)cccc3OC)cccc2c1N]

(4-amino-8-(2-fluoro-6-methoxy-phenyl)-N-propyl-cinnoline-3-carboxamide) or a pharmaceutically acceptable salt thereof;

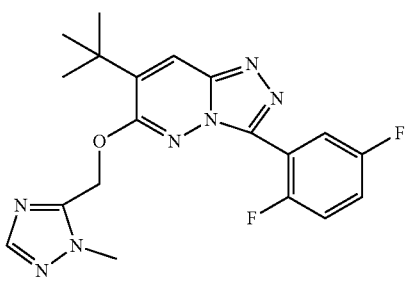 [SMILES: Cn1ncnc1COc1nn2c(-c3cc(F)ccc3F)nnc2cc1C(C)(C)C]

3-(2,5-Difluorophenyl)-7-(1,1-dimethylethyl)-6-[(1-methyl-1H-1,2,4-triazol-5-yl)methoxy]-1,2,4-triazolo[4,3-b]pyridazine or a pharmaceutically acceptable salt thereof; or combinations thereof.

In a further aspect, the compound may be a compound having alpha 2 and/or 3, partial agonist activity as described in WO1999037303 and/or U.S. Pat. No. 6,399,608 entitled "Combination of a GABA-A Alpha 2/3 agonist and a Selective Serotonin Reuptake Inhibitor" published Jul. 29, 1999).

In one aspect, the one or more signs and symptoms may be selected from impaired functional communication, anxiety, inattention, hyperactivity, sensory reactivity, autonomic nervous system dysregulation, aberrant eye gaze, self injury, aggression, seizures, EEG abnormalities including but not limited to abnormal spectral analysis, event related potentials which may include auditory and visual responses, abnormalities in cortical responses as evoked by transcranial magnetic stimulation including resting and active motor thresholds and abnormal responses in measures of cortical inhibition and excitation, aberrant impaired cognitive function, compromised daily living skills, or a combination thereof.

In one aspect, the GABA(A) alpha 2 and/or 3 partial agonist may be co-administered with co-administered with an agent selected from an atypical antipsychotics, lithium, a selective serotonin reuptake inhibitor (SSRI), a serotonin noradrenergic reuptake inhibitor (SNRI), non-SSRI non-SNRI serotonergic drug, a benzodiazepine, a glutamatergic drug, a GABA(B) modulator, opiate receptor modulators, endocannabinoid system modulators, a medication for the treatment of attention deficit hyperactivity disorder (ADHD), anti-epileptics, alpha 2-agonists, or a combination thereof.

In one aspect, the GABA(A) alpha 2 and/or 3 partial agonist may be co-administered with an agent selected from oxytocin, lithium, minocycline, or a combination thereof.

In one aspect, the GABA(A) alpha 2 and/or 3 partial agonist may be co-administered with structured non-drug therapies including occupational therapy, speech therapy, language learning interventions, social skills training, cognitive behavioral therapy, discrete trial training, biofeedback, computerized cognitive training, or a combination thereof.

In one aspect, the GABA(A) alpha 2 and/or 3 partial agonist may be administered in a dose of from about 2 g bid to about 15 g bid, or about 5 g bid to about 10 g bid.

In one aspect, the administration step may be carried out until ERK phosphorylation is normalized. The ERK phosphorylation normalization may be determined via measurement in the blood of a subject receiving said GABA(A) alpha 2 and/or 3 partial agonist.

Compositions

Compounds, or mixtures of compounds described herein, can be formulated into pharmaceutical composition comprising a pharmaceutically acceptable carrier and other excipients as apparent to the skilled worker. Such composition can additionally contain effective amounts of other compounds, especially for the treatment of conditions, diseases, and/or disorders described herein.

Some embodiments comprise the administration of a pharmaceutically effective quantity of active agent or its pharmaceutically acceptable salts or esters, active agent analogs or their pharmaceutically acceptable salts or esters, or a combination thereof.

The compositions and preparations may contain at least 0.1% of active agent. The percentage of the compositions and preparations can, of course, be varied, and can contain between about 2% and 60% of the weight of the amount administered. The percentage of the compositions and preparations may contain between about 2, 5, 10, or 15% and 30, 35, 40, 45, 50, 55, or 60% of the weight of the amount administered. The amount of active compounds in such pharmaceutically useful compositions and preparations is such that a suitable dosage will be obtained.

The disclosed active agents may form salts. Reference to a compound of the active agent herein is understood to include reference to salts thereof, unless otherwise indicated. The term "salt(s)", as employed herein, denotes acidic and/or basic salts formed with inorganic and/or organic acids and bases. In addition, when an active agent contains both a basic moiety, such as, but not limited to an amine or a pyridine or imidazole ring, and an acidic moiety, such as, but not limited to a carboxylic acid, zwitterions ("inner salts") can be formed and are included within the term "salt(s)" as used herein. Pharmaceutically acceptable (e.g., non-toxic, physiologically acceptable) salts are preferred, although other salts are also useful, e.g., in isolation or purification steps, which can be employed during preparation. Salts of the compounds of the active agent can be formed, for example, by reacting a compound of the active agent with an amount of acid or base, such as an equivalent amount, in a medium such as one in which the salt precipitates or in an aqueous medium followed by lyophilization.

Pharmaceutically acceptable salts include, but are not limited to, pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like.

The compounds can be formulated in various forms, including solid and liquid forms, such as tablets, gel, syrup, powder, aerosol, etc.

The compositions may contain physiologically acceptable diluents, fillers, lubricants, excipients, solvents, binders, stabilizers, and the like. Diluents that can be used in the compositions include but are not limited to dicalcium phosphate, calcium sulphate, lactose, cellulose, kaolin, mannitol, sodium chloride, dry starch, powdered sugar and for prolonged release tablet-hydroxy propyl methyl cellulose (HPMC). The binders that can be used in the compositions include but are not limited to starch, gelatin and fillers such as sucrose, glucose, dextrose and lactose.

Natural and synthetic gums that can be used in the compositions include but are not limited to sodium alginate, ghatti gum, carboxymethyl cellulose, methyl cellulose, polyvinyl pyrrolidone and veegum. Excipients that can be used in the compositions include but are not limited to microcrystalline cellulose, calcium sulfate, dicalcium phosphate, starch, magnesium stearate, lactose, and sucrose. Stabilizers that can be used include but are not limited to polysaccharides such as acacia, agar, alginic acid, guar gum and tragacanth, amphotsics such as gelatin and synthetic and semi-synthetic polymers such as carbomer resins, cellulose ethers and carboxymethyl chitin.

Solvents that can be used include but are not limited to Ringers solution, water, distilled water, dimethyl sulfoxide to 50% in water, propylene glycol (neat or in water), phosphate buffered saline, balanced salt solution, glycol and other conventional fluids.

The dosages and dosage regimen in which the compounds are administered will vary according to the dosage form, mode of administration, the condition being treated and particulars of the patient being treated. Accordingly, optimal therapeutic concentrations will be best determined at the time and place through routine experimentation.

The compounds may also be used enterally. Orally, the compounds may be administered at the rate of 100 µg to 100 mg per day per kg of body weight. Orally, the compounds may be suitably administered at the rate of about 100, 150, 200, 250, 300, 350, 400, 450, or 500 µg to about 1, 5, 10, 25, 50, 75, 100 mg per day per kg of body weight. The required dose can be administered in one or more portions. For oral administration, suitable forms are, for example, tablets, gel, aerosols, pills, dragees, syrups, suspensions, emulsions, solutions, powders and granules; one method of administration includes using a suitable form containing from 1 mg to about 500 mg of active substance. In one aspect, administration may comprise using a suitable form containing from about 1, 2, 5, 10, 25, or 50 mg to about 100, 200, 300, 400, 500 mg of active substance.

The compounds may also be administered parenterally in the form of solutions or suspensions for intravenous or intramuscular perfusions or injections. In that case, the compounds may be administered at the rate of about 10 µg to 10 mg per day per kg of body weight; one method of administration may consist of using solutions or suspensions containing approximately from 0.01 mg to 1 mg of active substance per ml. The compounds may be administered at the rate of about 10, 20, 30, 40, 50, 60, 70, 80, 90, or 100 µg to 1, 2, 3, 4, 5, 6, 7, 8, 9, or 10 mg per day per kg of body weight; in one aspect, solutions or suspensions containing approximately from 0.01, 0.02, 0.03, 0.04, or 0.5 mg to 0.1, 0.2, 0.3, 0.4, 0.5, 0.6, 0.7, 0.8, 0.9, or 1 mg of active substance per ml may be used.

The active compounds and/or pharmaceutical compositions of the embodiments disclosed herein can be administered according to various routes, such as by injection, for example local or systemic injection(s). Intratumoral injections maybe used. Other administration routes can be used as well, such as intramuscular, intravenous, intradermic, subcutaneous, etc. Furthermore, repeated injections can be performed, if needed, although it is believed that limited injections will be needed in view of the efficacy of the compounds.

For ex vivo administration, the active agent can be administered by any standard method that would maintain viability of the cells, such as by adding it to culture medium (appropriate for the target cells) and adding this medium directly to the cells. As is known in the art, any medium used in this method can be aqueous and non-toxic so as not to render the cells non-viable. In addition, it can contain standard nutrients for maintaining viability of cells, if desired. For in vivo administration, the complex can be added to, for example, to a pharmaceutically acceptable carrier, e.g., saline and buffered saline, and administered by any of several means known in the art. Examples of administration include parenteral administration, e.g., by intravenous injection including regional perfusion through a blood vessel supplying the tissues(s) or organ(s) having the target cell(s), or by inhalation of an aerosol, subcutaneous or intramuscular injection, topical administration such as to skin wounds and lesions, direct transfection into, e.g., bone marrow cells prepared for transplantation and subsequent transplantation into the subject, and direct transfection into an organ that is subsequently transplanted into the subject. Further administration methods include oral administration, particularly when the active agent is encapsulated, or rectal administration, particularly when the active agent is in suppository form.

It is contemplated that such target cells can be located within a subject or human patient, in which case a safe and effective amount of the active agent, in pharmacologically acceptable form, would be administered to the patient. Generally speaking, it is contemplated that useful pharmaceutical compositions may include the selected active compound derivative in a convenient amount, e.g., from about 0.001% to about 10% (w/w) that is diluted in a pharmacologically or physiologically acceptable carrier, such as, for example, phosphate buffered saline. The route of administration and ultimate amount of material that is administered to the subject under such circumstances will depend upon the intended application and will be apparent to those of skill in the art in light of the examples which follow.

Any composition chosen should be of low or non-toxicity to the cell. Toxicity for any given compound can vary with the concentration of compound used. It is also beneficial if the compound chosen is metabolized or eliminated by the body and if this metabolism or elimination is done in a manner that will not be harmfully toxic.

The compound may be administered such that a therapeutically effective concentration of the compound is in contact with the affected cells of the body. The dose administered to a subject, particularly a human, may be sufficient to effect a therapeutic response in the subject over a reasonable period of time. The dose may be determined by the strength of the particular compound employed and the condition of the subject, as well as the body weight of the subject to be treated. The existence, nature, and extent of any adverse side effects that might accompany the administration of a particular compound also will determine the size of the dose and the particular route of administration employed with a particular patient. In general, the compounds may be therapeutically effective at low doses. The generally useful dose range may be from about 0.001 mM, or less, to about 100 mM, or more. The effective dose range may be from about 0.01, 0.05, 0.1, 0.5, 0.6, 0.7, 0.8, or 0.9 mM, to about 1, 2, 3, 4, 5, 6, 7, 8, 9, or 10 mM. Accordingly, the compounds may be generally administered in low doses.

The pharmaceutical composition may further comprise a pharmaceutically acceptable carrier. The resulting preparation may incorporate, if necessary, one or more solubilizing agent, buffers, preservatives, colorants, perfumes, flavorings and the like that are widely used in the field of pharmaceutical preparation.

The proportion of the active ingredient to be contained in the disclosed compositions may be determined by one of ordinary skill in the art using art recognized methods.

The disclosed compounds may be formulated into a dosage form selected from the group consisting of tablets, capsules, granules, pills, injections, solutions, emulsions, suspensions, and syrups. The form and administration route for the pharmaceutical composition are not limited and can be suitably selected. For example, tablets, capsules, granules, pills, syrups, solutions, emulsions, and suspensions may be administered orally. Additionally, injections (e.g. subcutaneous, intravenous, intramuscular, and intraperitoneal) may be administered intravenously either singly or in combination with a conventional replenisher containing glucose, amino acid and/or the like, or may be singly administered intramuscularly, intracutaneously, subcutaneously and/or intraperitoneally.

The disclosed compositions may be prepared according to a method known in the pharmaceutical field of this kind using a pharmaceutically acceptable carrier. For example, oral forms such as tablets, capsules, granules, pills and the like are prepared according to known methods using excipients such as saccharose, lactose, glucose, starch, mannitol and the like; binders such as syrup, gum arabic, sorbitol, tragacanth, methylcellulose, polyvinylpyrrolidone and the like; disintegrates such as starch, carboxymethylcellulose or the calcium salt thereof, microcrystalline cellulose, polyethylene glycol and the like; lubricants such as talc, magnesium stearate, calcium stearate, silica and the like; and wetting agents such as sodium laurate, glycerol and the like.

Injections, solutions, emulsions, suspensions, syrups and the like may be prepared according to a known method suitably using solvents for dissolving the active ingredient, such as ethyl alcohol, isopropyl alcohol, propylene glycol, 1,3-butylene glycol, polyethylene glycol, sesame oil and the like; surfactants such as sorbitan fatty acid ester, polyoxyethylenesorbitan fatty acid ester, polyoxyethylene fatty acid ester, polyoxyethylene of hydrogenated castor oil, lecithin and the like; suspending agents such as cellulose derivatives including carboxymethylcellulose sodium, methylcellulose and the like, natural gums including tragacanth, gum arabic and the like; and preservatives such as parahydroxybenzoic acid esters, benzalkonium chloride, sorbic acid salts and the like.

The compounds can be administered orally, topically, parenterally, by inhalation or spray, vaginally, rectally, nasally, or sublingually. The compounds may be administered in dosage unit formulations. The term "administration by injection" includes but is not limited to: intravenous, intraarticular, intramuscular, subcutaneous and parenteral injections, as well as use of infusion techniques. Dermal administration can include topical application or transdermal administration. One or more compounds can be present in association with one or more non-toxic pharmaceutically acceptable carriers and if desired other active ingredients.

Compositions intended for oral use can be prepared according to any suitable method known to the art for the manufacture of pharmaceutical compositions. Such compositions can contain one or more agents selected from the group consisting of diluents, sweetening agents, flavoring agents, coloring agents and preserving agents in order to provide palatable preparations. Tablets contain the active ingredient in admixture with non-toxic pharmaceutically acceptable excipients that are suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; and binding agents, for example magnesium stearate, stearic acid or talc. The tablets can be uncoated or they can be coated by known techniques to delay disintegration and adsorption in the gastrointestinal tract and thereby provide a sustained action over a longer period. For example, a time delay material such as glyceryl monostearate or glyceryl distearate can be employed. These compounds can also be prepared in solid, rapidly released form.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions containing the active materials in admixture with excipients suitable for the manufacture of aqueous suspensions can also be used. Such excipients are suspending agents, for example sodium carboxymethylcellulose, methylcellulose, hydroxypropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethylene oxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, can also be present.

The compounds can also be in the form of non-aqueous liquid formulations, e.g., oily suspensions which can be formulated by suspending the active ingredients in a vegetable oil, for example arachis oil, olive oil, sesame oil or peanut oil, or in a mineral oil such as liquid paraffin. The oily suspensions can contain a thickening agent, for example beeswax, hard paraffin or cetyl alcohol. Sweetening agents such as those set forth above, and flavoring agents can be added to provide palatable oral preparations. These compositions can be preserved by the addition of an anti-oxidant such as ascorbic acid.

Compounds may also be administered transdermally using methods known to those skilled in the art. For example, a solution or suspension of an active agent in a suitable volatile solvent optionally containing penetration enhancing agents can be combined with additional additives known to those skilled in the art, such as matrix materials and bacteriocides. After sterilization, the resulting mixture can be formulated following known procedures into dosage forms. In addition, on treatment with emulsifying agents and water, a solution or suspension of an active agent can be formulated into a lotion or salve.

Suitable solvents for processing transdermal delivery systems are known to those skilled in the art, and include lower alcohols such as ethanol or isopropyl alcohol, lower ketones such as acetone, lower carboxylic acid esters such as ethyl acetate, polar ethers such as tetrahydrofuran, lower hydrocarbons such as hexane, cyclohexane or benzene, or halogenated hydrocarbons such as dichloromethane, chloroform, trichlorotrifluoroethane, or trichlorofluoroethane. Suitable solvents can also include mixtures of one or more materials selected from lower alcohols, lower ketones, lower carboxylic acid esters, polar ethers, lower hydrocarbons, halogenated hydrocarbons.

Suitable penetration enhancing materials for transdermal delivery system are known to those skilled in the art, and include, for example, monohydroxy or polyhydroxy alcohols such as ethanol, propylene glycol or benzyl alcohol, saturated or unsaturated C8-C18 fatty alcohols such as lauryl alcohol or cetyl alcohol, saturated or unsaturated C8-C18 fatty acids such as stearic acid, saturated or unsaturated fatty esters with up to 24 carbons such as methyl, ethyl, propyl, isopropyl, n-butyl, sec-butyl, isobutyl, tertbutyl or monoglycerin esters of acetic acid, capronic acid, lauric acid, myristinic acid, stearic acid, or palmitic acid, or diesters of saturated or unsaturated dicarboxylic acids with a total of up to about 24 carbons such as diisopropyl adipate, diisobutyl adipate, diisopropyl sebacate, diisopropyl maleate, or diisopropyl fumarate. Additional penetration enhancing materials include phosphatidyl derivatives such as lecithin or cephalin, terpenes, amides, ketones, ureas and their derivatives, and ethers such as dimethyl isosorbid and diethyleneglycol monoethyl ether. Suitable penetration enhancing formulations can also include mixtures of one or more materials selected from monohydroxy or polyhydroxy alcohols, saturated or unsaturated C8-C18 fatty alcohols, saturated or unsaturated C8-C18 fatty acids, saturated or unsaturated fatty esters with up to 24 carbons, diesters of saturated or unsaturated discarboxylic acids with a total of up to 24 carbons, phosphatidyl derivatives, terpenes, amides, ketones, ureas and their derivatives, and ethers.

Suitable binding materials for transdermal delivery systems are known to those skilled in the art and include polyacrylates, silicones, polyurethanes, block polymers, styrenebutadiene copolymers, and natural and synthetic rubbers. Cellulose ethers, derivatized polyethylenes, and silicates can also be used as matrix components. Additional additives, such as viscous resins or oils can be added to increase the viscosity of the matrix.

Pharmaceutical compositions may also be in the form of oil-in-water emulsions. The oil phase can be a vegetable oil, for example olive oil or arachis oil, or a mineral oil, for example, liquid paraffin or mixtures of these. Suitable emulsifying agents can be naturally-occurring gums, for example, gum acacia or gum tragacanth, naturally-occurring phosphatides, for example, soy bean, lecithin, and esters or partial esters derived from fatty acids and hexitol anhydrides, for example, sorbitan monooleate, and condensation products of the said partial esters with ethylene oxide, for example, polyoxyethylene sorbitan monooleate. The emulsions can also contain sweetening and flavoring agents. Syrups and elixirs can be formulated with sweetening agents, for example glycerol, propylene glycol, sorbitol or sucrose. Such formulations can also contain a demulcent, a preservative and flavoring and coloring agents.

The compounds can also be administered in the form of suppositories for rectal or vaginal administration of the drug. These compositions can be prepared by mixing the drug with a suitable nonirritating excipient which is solid at ordinary temperatures but liquid at the rectal temperature or vaginal temperature and will therefore melt in the rectum or vagina to release the drug. Such materials include cocoa butter and polyethylene glycols.

The compositions may be further administered intranasally. In such aspect, the compositions may further comprise other agents suited for improved delivery across nasal mucosa. For example, in certain aspects, agents such as a permeation enhancer, a polymer capable of increasing mucosal adhesion of the composition, or a combination thereof may be included in the composition.

It will be appreciated by those skilled in the art that the particular method of administration will depend on a variety of factors, all of which are considered routinely when administering therapeutics. It will also be understood, however, that the specific dose level for any given patient will depend upon a variety of factors, including, the activity of the specific compound employed, the age of the patient, the body weight of the patient, the general health of the patient, the gender of the patient, the diet of the patient, time of administration, route of administration, rate of excretion, drug combinations, and the severity of the condition undergoing therapy. It will be further appreciated by one skilled in the art that the optimal course of treatment, i.e., the mode of treatment and the daily number of doses of an active agent or a pharmaceutically acceptable salt thereof given for a defined number of days, can be ascertained by those skilled in the art using conventional treatment tests.

EXAMPLES

As a validated model of FXS, Fmr1 KO mice exhibit altered responses to sensory stimuli (auditory, pain, etc.), and learning impairments. Additionally they also exhibit aberrant ERK1/2 activation along with abnormal dendritic spines and altered synaptic plasticity. AZD7325, 4-amino-8-(2-fluoro-6-methoxy-phenyl)-N-propyl-cinnoline-3-carboxamide, is a potent selective partial GABA(A) α2,3 receptor agonist developed by AstraZeneca (AZ) for the treatment of anxiety, having the following structure:

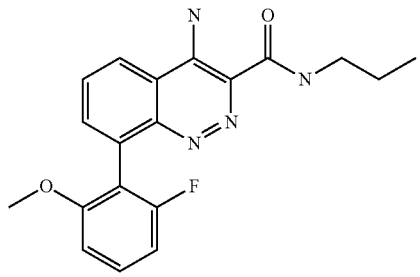 [SMILES: CCCNC(=O)c1nnc2c(-c3c(F)cccc3OC)cccc2c1N]

Throughout experiments in Fmr1 KO mice, we treated animals with 1 mg/kg AZD7325, 3 mg/kg AZD7325 or vehicle (VEH) by oral gavage to mimic the human exposure route. Juvenile mice were treated acutely and adult mice were treated chronically prior to and throughout behavior analysis. Data were analyzed by 2-way ANOVA unless otherwise indicated. *p≤0.05 indicates significantly different than WT+VEH group.

Figure 2:
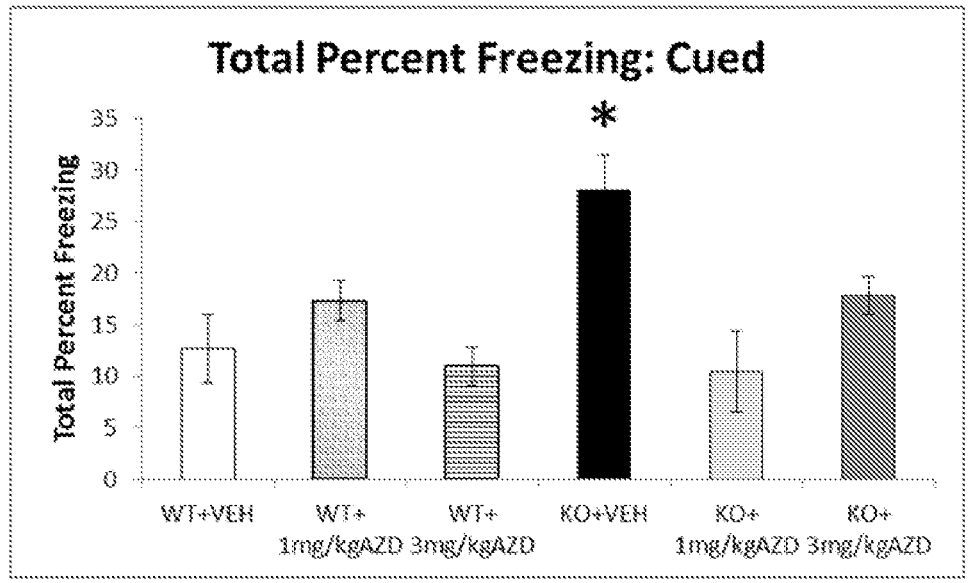
FIG. 2 shows that the conditioned fear responses to a mild foot shock were shown to be exaggerated in Fragile X Syndrome KO mice compared to WT mice during the cued portion of the test with 4-amino-8-(2-fluoro-6-methoxy-phenyl)-N-propyl-cinnoline-3-carboxamide ("AZD7325") treatment at both dose levels normalizing this behavior in KO mice.
Figure 3:
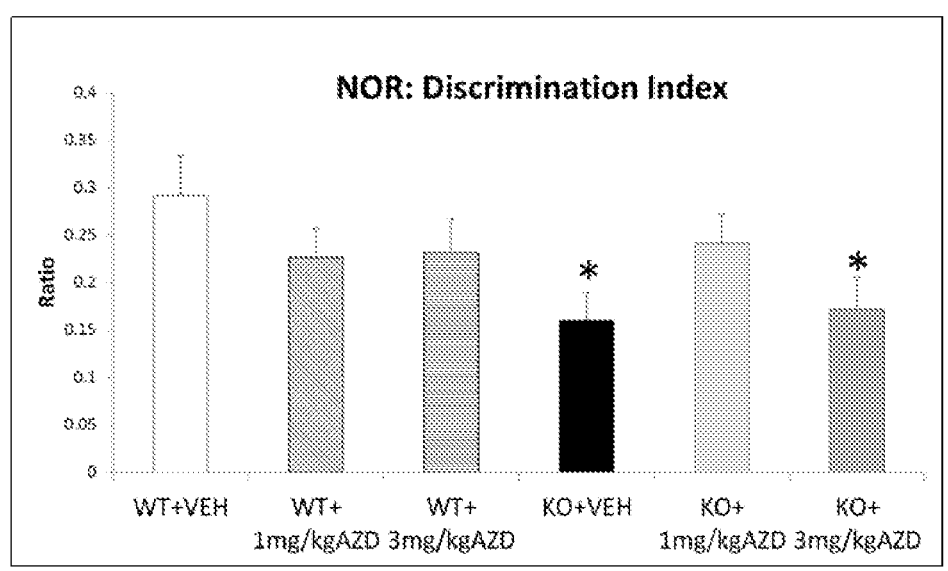
FIG. 3 shows the results of treatment with low dose AZD7325 improves memory in Fragile X Syndrome KO mice. Such treatment attenuates deficits in object memory when assessed in a novel object recognition paradigm indicated by an increase in discrimination index ratio (DI) in the low dose KO mice (FIG. 3; main effect of genotype for discrimination index (F(1.86)=4.99, P<0.03)).
Figure 4:
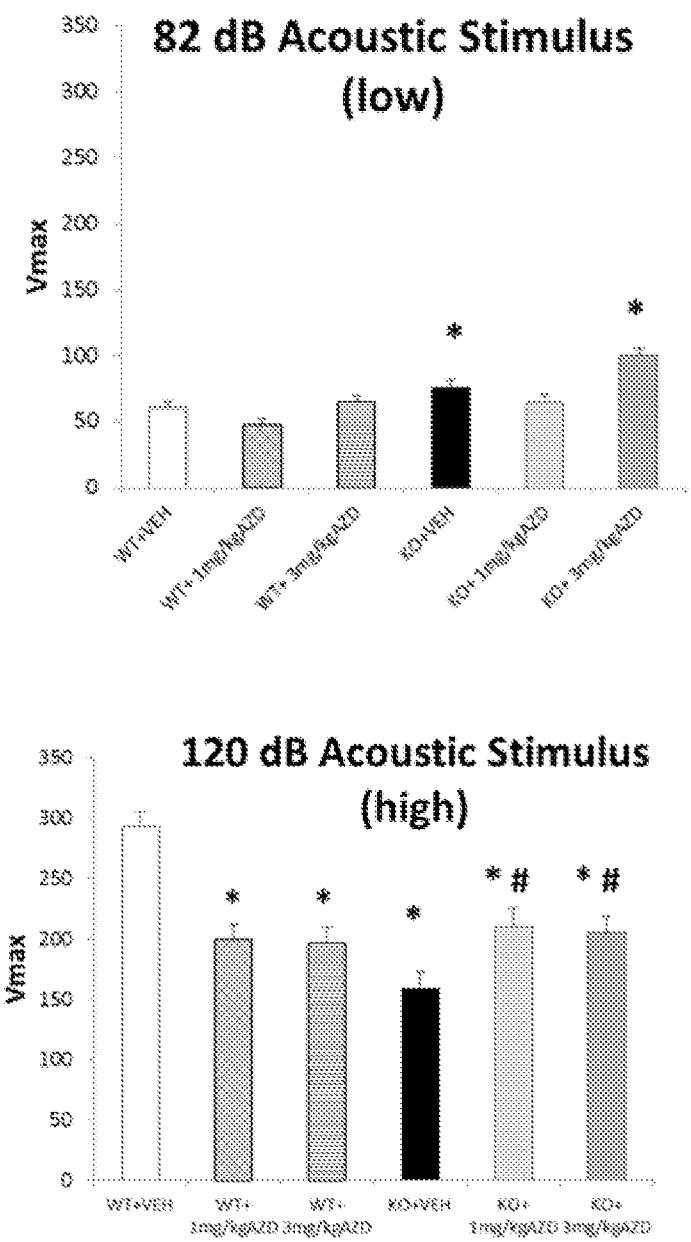
FIG. 4 shows that the response to acoustic stimuli in KO mice is corrected and response to intensity is appropriately gated with AZD7325 treatment. In adulthood, Fmr1 KO mice have abnormal motor responses to sensory stimuli compared to WT mice in an acoustic startle paradigm. When presented with a short low level white noise burst (82 db) over 10 trial blocks, Fmr1 KO mice will flinch at a higher amplitude than WT mice (presentation of these startle bursts do not elicit seizure activity).

Audiogenic seizure susceptibility in Fmr1 KO mice, which is thought to be the result of increased neuronal activity in response to sensory stimuli, peaks around the third week of life and manifests as wild running which is typically followed by tonic-clonic seizure. WT mice do not respond to this siren with any noticeable running or seizure behavior. FIG. 1 shows that approximately 60% Fmr1 KO mice treated with VEH displayed wild running followed by seizure in response to a loud stimulus (120 dB siren), but when treated acutely (30 min prior to testing) with both the low (11%) and high (0%) dose of 4-amino-8-(2-fluoro-6-methoxy-phenyl)-N-propyl-cinnoline-3-carboxamide, seizure activity was significantly reduced, indicating that the drug is reducing hyperexcitability in the brain (Fisher's exact test p<0.0002). In adulthood, Fmr1 KO mice have abnormal motor responses to sensory stimuli compared to WT mice in an acoustic startle paradigm. When presented with a short low level white noise burst (82 db) over 10 trial blocks, Fmr1 KO mice will flinch at a higher amplitude than WT mice (presentation of these startle bursts do not elicit seizure activity). FIG. 4; top main effect of genotype (P<0.001) and drug (P<0.0001) for Vmax) shows that Fmr1 KO mice treated chronically with the low dose of AZD7325 have significantly reduced whole body flinching in this low-level Acoustic startle paradigm. Interestingly, in a paradigm employing a high level acoustic stimulus (120 dB), adult Fmr1 KO mice will repeatedly respond to the stimulus with a lower amplitude whole body flinch compared to WT mice. FIG. 4; bottom (Gene x Drug interaction P<0.0001) shows that treatment with AZD7325 improves this response to WT levels demonstrating that drug treatment isn't simply reducing overall whole body flinching in response to sensory stimuli, but is rather mediating responses so that they are becoming more appropriate and reflective of startle intensity. *P indicates significantly different from WT+VEH; #P indicates significantly different from KO+VEH. Conditioned fear responses to a mild foot shock were shown to be exaggerated compared to WT mice during the cued portion of the test with 4-amino-8-(2-fluoro-6-methoxy-phenyl)-N-propyl-cinnoline-3-carboxamide treatment at both dose levels normalizing this behavior in KO mice (FIG. 2; main effect of genotype (F(1.20)=4.26, P<0.05), and gene×drug interaction (F(2.20)=7.79, P<0.003)). This type of deficit in the VEH-treated Fmr1 KO mice is reminiscent of the exaggerated anxiety responses people with FXS commonly display. Treatment with the low dose of 4-amino-8-(2-fluoro-6-methoxy-phenyl)-N-propyl-cinnoline-3-carboxamide also attenuates deficits in object memory when assessed in a novel object recognition paradigm (FIG. 3; main effect of genotype for discrimination index (F(1.86)=4.99, P<0.03)).

Low dose-treated animals showed greater interest in the novel object during the second phase compared to VEH-treated KO mice indicating a greater memory of the familiar object which was introduced during the first phase of the test. Based upon preclinical data in FXS implicating insufficient GABA(A) activity in the pathophysiology of the disorder combined with preclinical and human evidence (unpublished data) supporting the tolerability and effectiveness of improving aberrant behavior, 4-amino-8-(2-fluoro-6-methoxy-phenyl)-N-propyl-cinnoline-3-carboxamide is an ideal molecule to develop as a clinical treatment in humans with FXS.

REFERENCES

1. D'Hulst C, De Geest N, Reeve S P, et al. Decreased expression of the GABAA receptor in fragile X syndrome. Brain research 2006; 1121:238-45.
2. D'Hulst C, Kooy R F. The GABAA receptor: a novel target for treatment of fragile X? Trends in neurosciences 2007; 30:425-31.

3. Olmos-Serrano J L, Corbin J G, Burns M P. The GABA (A) receptor agonist THIP ameliorates specific behavioral deficits in the mouse model of fragile X syndrome. Developmental neuroscience 2011; 33:395-403.
4. Olmos-Serrano J L, Paluszkiewicz S M, Martin B S, Kaufmann W E, Corbin J G, Huntsman M M. Defective GABAergic neurotransmission and pharmacological rescue of neuronal hyperexcitability in the amygdala in a mouse model of fragile X syndrome. The Journal of neuroscience: the official journal of the Society for Neuroscience 2010; 30:9929-38.
5. Heulens I, D'Hulst C, Van Dam D, De Deyn P P, Kooy R F. Pharmacological treatment of fragile X syndrome with GABAergic drugs in a knockout mouse model. Behavioural brain research 2012; 229:244-9.
6. Jacquemont S, Curie A, des Portes V, et al. Epigenetic modification of the FMR1 gene in fragile X syndrome is associated with differential response to the mGluR5 antagonist AFQ056. Science translational medicine 2011; 3:64ra1.
7. Berry-Kravis E M, Hessl D, Rathmell B, et al. Effects of STX209 (Arbaclofen) on Neurobehavioral Function in Children and Adults with Fragile X Syndrome: A Randomized, Controlled, Phase 2 Trial. Sci Transl Med 2012; 4:152ra27.
8. Heulens I, D'Hulst C, Braat S, Rooms L, Kooy R F. Involvement and therapeutic potential of the GABAergic system in the fragile X syndrome. ScientificWorldJournal 2010; 10:2198-206.
9. Hong A, Zhang A, Ke Y, El Idrissi A, Shen C H. Downregulation of GABA(A) beta subunits is transcriptionally controlled by Fmr1p. J Mol Neurosci 2012; 46:272-5.
10. D'Hulst C, Heulens I, Brouwer J R, et al. Expression of the GABAergic system in animal models for fragile X syndrome and fragile X associated tremor/ataxia syndrome (FXTAS). Brain research 2008.
11. El Idrissi A, Ding X H, Scalia J, Trenkner E, Brown W T, Dobkin C. Decreased GABA(A) receptor expression in the seizure-prone fragile X mouse. Neuroscience letters 2005; 377:141-6.
12. El Idrissi A, Yan X, L'Amoreaux W, Brown W T, Dobkin C. Neuroendocrine alterations in the fragile X mouse. Results Probl Cell Differ 2012; 54:201-21.
13. Hagerman R J, Sobesky W E. Psychopathology in fragile X syndrome. The American journal of orthopsychiatry 1989; 59:142-52.
14. Sobesky W E, Pennington B F, Porter D, Hull C E, Hagerman R J. Emotional and neurocognitive deficits in fragile X. Am J Med Genet 1994; 51:378-85.
15. Hagerman R J, Hills J, Scharfenaker S, Lewis H. Fragile X syndrome and selective mutism. Am J Med Genet 1999; 83:313-7.
16. Berry-Kravis E, Potanos K. Psychopharmacology in fragile X syndrome—present and future. Ment Retard Dev Disabil Res Rev 2004; 10:42-8.
17. Angkustsiri K, Wirojanan J, Deprey U, Gane L W, Hagerman R J. Fragile X syndrome with anxiety disorder and exceptional verbal intelligence. Am J Med Genet A 2008; 146:376-9.
18. Shanahan M, Roberts J, Hatton D, Remick J, Goldsmith H. Early temperament and negative reactivity in boys with fragile X syndrome. J Intellect Disabil Res 2008; 52:842-54.
19. Bailey D B, Jr., Raspa M, Bishop E, Olmsted M, Mallya U G, Berry-Kravis E. Medication utilization for targeted symptoms in children and adults with fragile X syndrome: US survey. Journal of developmental and behavioral pediatrics: JDBP 2012; 33:62-9.
20. Tranfaglia M R. Fragile X syndrome: a psychiatric perspective. Results Probl Cell Differ 2012; 54:281-95.
21. Erickson C A, Stigler K A, Posey D, McDougle C. Managing maladaptive behaviors in fragile X patients. Curr Psychiatry 2006; 5:80-92.
22. Rudolph U, Knoflach F. Beyond classical benzodiazepines: novel therapeutic potential of GABAA receptor subtypes. Nature reviews Drug discovery 2011; 10:685-97.
23. Alhambra C, Becker C, Blake T, et al. Development and SAR of functionally selective allosteric modulators of GABAA receptors. Bioorganic & medicinal chemistry 2011; 19:2927-38.
24. Kuribara H, Asahi T. Assessment of the anxiolytic and amnesic effects of three benzodiazepines, diazepam, alprazolam and triazolam, by conflict and non-matching to sample tests in mice. Nihon shinkei seishin yakurigaku zasshi=Japanese journal of psychopharmacology 1997; 17:1-6.
25. Zhou D, Sunzel M, Ribadeneira M D, et al. A clinical study to assess CYP1A2 and CYP3A4 induction by AZD7325, a selective GABA(A) receptor modulator—an in vitro and in vivo comparison. Br J Clin Pharmacol 2012; 74:98-108.
26. Henderson C, Wijetunge L, Kinoshita M N, et al. Reversal of disease-related pathologies in the fragile X mouse model by selective activation of GABA(B) receptors with arbaclofen. Science translational medicine 2012; 4:152ra28.
27. Kooy R F, D'Hooge R, Reyniers E, et al. Transgenic mouse model for the fragile X syndrome. Am J Med Genet 1996; 64:241-5.
28. Chen L, Toth M. Fragile X mice develop sensory hyperreactivity to auditory stimuli. Neuroscience 2001; 103:1043-50.
29. Romero-Zerbo Y, Decara J, el Bekay R, et al. Protective effects of melatonin against oxidative stress in Fmr1 knockout mice: a therapeutic research model for the fragile X syndrome. Journal of pineal research 2009; 46:224-34.
30. Mientjes E J, Nieuwenhuizen I, Kirkpatrick L, et al. The generation of a conditional Fmr1 knock out mouse model to study Fmrp function in vivo. Neurobiology of disease 2006; 21:549-55.
31. Liu Z H, Smith C B. Dissociation of social and nonsocial anxiety in a mouse model of fragile X syndrome. Neuroscience letters 2009; 454:62-6.
32. Moon J, Beaudin A E, Verosky S, et al. Attentional dysfunction, impulsivity, and resistance to change in a mouse model of fragile X syndrome. Behavioral neuroscience 2006; 120:1367-79.
33. Schaefer T L, Vorhees C V, Williams M T. Mouse plasmacytoma-expressed transcript 1 knock out induced 5-H T disruption results in a lack of cognitive deficits and an anxiety phenotype complicated by hypoactivity and defensiveness. Neuroscience 2009; 164:1431-43.
34. Schaefer T L, Lingrel J B, Moseley A E, Vorhees C V, Williams M T. Targeted mutations in the Na,K-ATPase alpha 2 isoform confer ouabain resistance and result in abnormal behavior in mice. Synapse 2011; 65:520-31.
35. Thomas A, Burant A, Bui N, Graham D, Yuva-Paylor L A, Paylor R. Marble burying reflects a repetitive and perseverative behavior more than novelty-induced anxiety. Psychopharmacology (Berl) 2009; 204:361-73.

36. Veeraragavan S, Graham D, Bui N, Yuva-Paylor L A, Wess J, Paylor R. Genetic reduction of muscarinic M4 receptor modulates analgesic response and acoustic startle response in a mouse model of fragile X syndrome (FXS). Behavioural brain research 2012; 228:1-8.
37. Thomas A M, Bui N, Perkins J R, Yuva-Paylor L A, Paylor R. Group I metabotropic glutamate receptor antagonists alter select behaviors in a mouse model for fragile X syndrome. Psychopharmacology (Berl) 2012; 219:47-58.
38. Egashira N, Abe M, Shirakawa A, et al. Effects of mood stabilizers on marble-burying behavior in mice: Involvement of GABAergic system. Psychopharmacology (Berl) 2012.
39. Goebel-Goody S M, Wilson-Wallis E D, Royston S, Tagliatela S M, Naegele J R, Lombroso P J. Genetic manipulation of STEP reverses behavioral abnormalities in a fragile X syndrome mouse model. Genes, brain, and behavior 2012; 11:586-600.
40. Bourin M, Hascoet M. The mouse light/dark box test. European journal of pharmacology 2003; 463:55-65.
41. Crawley J, Goodwin F K. Preliminary report of a simple animal behavior model for the anxiolytic effects of benzodiazepines. PharmacolBiochemBehav 1980; 13:167-70.
42. Frankland P W, Wang Y, Rosner B, et al. Sensorimotor gating abnormalities in young males with fragile X syndrome and Fmr1-knockout mice. Molecular psychiatry 2004; 9:417-25.
43. Dahlhaus R, El-Husseini A. Altered neuroligin expression is involved in social deficits in a mouse model of the fragile X syndrome. Behavioural brain research 2010; 208:96-105.
44. Bhattacharya A, Kaphzan H, Alvarez-Dieppa A C, Murphy J P, Pierre P, Klann E. Genetic removal of p70 S6 kinase 1 corrects molecular, synaptic, and behavioral phenotypes in fragile X syndrome mice. Neuron 2012; 76:325-37.
45. Dunlop B W, Papp L, Garlow S J, Weiss P S, Knight B T, Ninan P T. Tiagabine for social anxiety disorder. Human psychopharmacology 2007; 22:241-4.
46. Skelton M R, Schaefer T L, Graham D L, et al. Creatine transporter (CrT; Slc6a8) knockout mice as a model of human CrT deficiency. PLoS One 2011; 6:e16187.
47. Brunskill E W, Ehrman L A, Williams M T, et al. Abnormal neurodevelopment, neurosignaling and behaviour in Npas3-deficient mice. EurJNeurosci 2005; 22:1265-76.
48. Lindzey G, Winston H, Manosevitz M. Social dominance in inbred mouse strains. Nature 1961; 191:474-6.
49. Spencer C M, Alekseyenko 0, Serysheva E, Yuva-Paylor L A, Paylor R. Altered anxiety-related and social behaviors in the Fmr1 knockout mouse model of fragile X syndrome. Genes Brain Behav 2005; 4:420-30.
50. D'Hooge R, Nagels G, Franck F, et al. Mildly impaired water maze performance in male Fmr1 knockout mice. Neuroscience 1997; 76:367-76.
51. Williams M T, Brown R W, Vorhees C V. Neonatal methamphetamine administration induces region-specific long-term neuronal morphological changes in the rat hippocampus, nucleus accumbens and parietal cortex. The European journal of neuroscience 2004; 19:3165-70.
52. Gibb R, Kolb B. A method for vibratome sectioning of Golgi-Cox stained whole rat brain. Journal of neuroscience methods 1998; 79:1-4.
53. Sholl D A. The Organization of the Cerebral Cortex. London: Methuen & Co. ; 1956.
54. Shimono K, Baudry M, Ho L, Taketani M, Lynch G. Long-term recording of LTP in cultured hippocampal slices. Neural plasticity 2002; 9:249-54.
55. Curran C P, Nebert D W, Genter M B, et al. In utero and lactational exposure to PCBs in mice: adult offspring show altered learning and memory depending on Cyp1a2 and Ahr genotypes. Environ Health Perspect 2011; 119: 1286-93.
56. Hochberg Y, Benjamini Y. More powerful procedures for multiple significance testing. Statistics in medicine 1990; 9:811-8.

What is claimed is:

1. A method of alleviating autonomic nervous system dysregulation associated with fragile X, comprising administering to a subject in need thereof, a therapeutically effective amount of

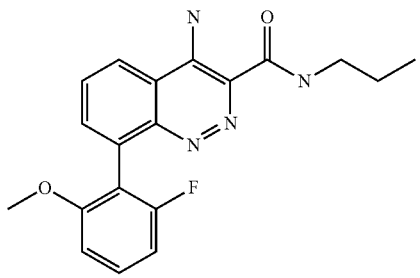 [SMILES: CCCNC(=O)c1nnc2c(-c3c(F)cccc3OC)cccc2c1N]

4-amino-8-(2-fluoro-6-methoxy-phenyl)-N-propyl-cinnoline-3-carboxamide) or pharmaceutically acceptable salt thereof.

2. The method of claim 1, wherein said administration alleviates one or more of impaired functional communication, anxiety, inattention, hyperactivity, sensory reactivity, aberrant eye gaze, self-injury, aggression, seizures, EEG abnormalities, abnormal auditory and visual responses, abnormalities in cortical responses as evoked by transcranial magnetic stimulation, abnormal responses in measures of cortical inhibition and excitation, aberrant impaired cognitive function, compromised daily living skills, or a combination thereof.

3. The method of claim 1, wherein said (4-amino-8-(2-fluoro-6-methoxy-phenyl)-N-propyl-cinnoline-3-carboxamide) is co-administered with an agent selected from an atypical antipsychotic, lithium, a selective serotonin reuptake inhibitor (SSRI), a serotonin noradrenergic reuptake inhibitor (SNRI), non-SSRI non-SNRI serotonergic drug, a benzodiazepine, a glutamatergic drug, a GABA (B) modulator, opiate receptor modulators, endocannabinoid system modulators, a medication for the treatment of attention deficit hyperactivity disorder (ADHD), anti-epileptics, alpha 2-agonists, mGlur5 antagonists, glutamatergic agents, GABA modulators, or a combination thereof.

4. The method of claim 1, wherein said (4-amino-8-(2-fluoro-6-methoxy-phenyl)-N-propyl-cinnoline-3-carboxamide) is co-administered with an agent selected from oxytocin, lithium, minocycline, or a combination thereof.

5. The method of claim 1, wherein said (4-amino-8-(2-fluoro-6-methoxy-phenyl)-N-propyl-cinnoline-3-carboxamide) is co-administered with a structured non-drug therapy selected from occupational therapy, speech therapy, a language learning intervention, social skills training, cognitive behavioral therapy, discrete trial training, biofeedback, computerized cognitive training, or a combination thereof.

6. The method of claim 1, wherein said (4-amino-8-(2-fluoro-6-methoxy-phenyl)-N-propyl-cinnoline-3-carboxamide) is administered orally.

7. The method of claim 6, wherein said (4-amino-8-(2-fluoro-6-methoxy-phenyl)-N-propyl-cinnoline-3-carboxamide) is formulated into a dosage form selected from the group consisting of tablets, capsules, granules, pills, injections, solutions, emulsions, suspensions, and syrups.

8. The method of claim 7, wherein the (4-amino-8-(2-fluoro-6-methoxy-phenyl)-N-propyl-cinnoline-3-carboxamide) is administered in a dosage form containing from about 1 to 500 mg.

9. The method of claim 8, wherein the dosage form contains from about 1, 2, 5, 10, 25, 50, 100, 200, 300, 400, or 500 mg.

10. The method of claim 7, wherein the (4-amino-8-(2-fluoro-6-methoxy-phenyl)-N-propyl-cinnoline-3-carboxamide) is administered in a dosage form twice daily (bid).

11. The method of claim 1, wherein said (4-amino-8-(2-fluoro-6-methoxy-phenyl)-N-propyl-cinnoline-3-carboxamide) is administered nasally.

12. The method of claim 1, wherein said administration step is carried out until ERK phosphorylation is normalized.

* * * * *